(12) United States Patent
Hirao et al.

(10) Patent No.: US 9,857,362 B2
(45) Date of Patent: Jan. 2, 2018

(54) METHOD FOR PREPARING NUCLEIC ACID APTAMER

(71) Applicant: TAGCYX BIOTECHNOLOGIES, Yokohama-shi, Kanagawa (JP)

(72) Inventors: Ichiro Hirao, Kanagawa (JP); Michiko Hirao, Kanagawa (JP); Shigeyuki Yokoyama, Kanagawa (JP)

(73) Assignee: TAGCYX BIOTECHNOLOGIES, Kanagawa (JP)

( * ) Notice: Subject to any disclaimer, the term of this patent is extended or adjusted under 35 U.S.C. 154(b) by 0 days.

(21) Appl. No.: 15/188,297

(22) Filed: Jun. 21, 2016

(65) Prior Publication Data

US 2016/0289680 A1    Oct. 6, 2016

Related U.S. Application Data

(62) Division of application No. 14/237,645, filed as application No. PCT/JP2012/070188 on Aug. 8, 2012.

(30) Foreign Application Priority Data

Aug. 12, 2011    (JP) ................................ 2011-177112

(51) Int. Cl.
| | | |
|---|---|---|
| *C12N 15/115* | (2010.01) |
| *G01N 33/543* | (2006.01) |
| *C12N 15/10* | (2006.01) |
| *G01N 33/53* | (2006.01) |
| *A61K 31/7105* | (2006.01) |
| *C12Q 1/68* | (2006.01) |

(52) U.S. Cl.
CPC ....... *G01N 33/543* (2013.01); *A61K 31/7105* (2013.01); *C12N 15/1048* (2013.01); *C12N 15/115* (2013.01); *C12Q 1/6834* (2013.01); *G01N 33/5308* (2013.01); *C12N 2310/16* (2013.01); *C12N 2320/13* (2013.01); *C12N 2320/30* (2013.01); *C12N 2330/30* (2013.01); *G01N 2333/47* (2013.01); *G01N 2333/4703* (2013.01)

(58) Field of Classification Search
None
See application file for complete search history.

(56) References Cited

U.S. PATENT DOCUMENTS

| | | |
|---|---|---|
| 2004/0171077 A1 | 9/2004 | Lubenow et al. |
| 2006/0281076 A1 | 12/2006 | Marla et al. |
| 2009/0170219 A1 | 7/2009 | Nakamura et al. |
| 2011/0144187 A1 | 6/2011 | Wang et al. |
| 2011/0177578 A1 | 7/2011 | Nakamura et al. |

FOREIGN PATENT DOCUMENTS

| | | |
|---|---|---|
| CN | 102099471 A | 6/2011 |
| WO | WO 91/14842 A1 | 12/1991 |
| WO | WO 92/14843 A1 | 9/1992 |
| WO | WO 94/08050 A1 | 4/1994 |
| WO | WO 96/40159 A1 | 12/1996 |
| WO | WO 02/077262 A2 | 10/2002 |

OTHER PUBLICATIONS

Plieur et al (Nucleic Acids Research 31(19): 5776-5788, 2003).*
Cassiday et al (Biochemistry 2001, 40: 2433-2438).*
Hirao, Ichiro, "Synthetic biology for the development of novel nucleic acid aptamers," Cytometry Research, 2009, 19(2):9-17.
Pierce Biotechnology, "Streptavidin UltraLink® Resin," 2008, http://www.funakoshi.co.jp.data.datasheet/PCC/53114.pdf.
Bock et al., "Selection of single-stranded DNA molecules that bind and inhibit human thrombin," Nature, Feb. 6, 1992, 355:564-566.
Cho et al., "Quantitative selection of DNA aptamers through microfluidic selection and high-throughput sequencing," PNAS, Aug. 31, 2010, 107(35):15373-15378.
Fan et al., "Probing TBP interactions in transcription initiation and reinitiation with RNA aptamers that act in distinct modes," PNAS, May 4, 2004, 101(18):6934-6939.
Fujii et al., "FOXK2 transcription factor is a novel G/T-mismatch DNA binding protein," J. Biochem., Jan. 22, 2010, 147(5):705-709.
Hamula et al., "Selection of Aptamers against Live Bacterial Cells," Anal. Chem., 2008, 80:7812-7819.
Hermann et al., "Non-Watson-Crick base pairs in RNA-protein recognition," Chemistry & Biology, 1999, 6:R335-R343.
Jeong et al., "Identification of RNA Aptamer Specific to Mutant KRAS Protein," Oligonucleotides, 2010, 20(3):155-161.
Lauhon et al., "RNA Aptamers That Bind Flavin and Nicotinamide Redox Cofactors," J. Am. Chem. Soc., 1995, 117:1246-1257.
Orava et al., "Delivering cargoes into cancer cells using DNA aptamers targeting internatlized surface portals," Biochimica et Biophysica Acta, 2010, 1798(12):2190-2200.
Pierce Biotechnology, "Straptavidin UltraLink® Resin," 2008, http://www.funakoshi.co.jp.data.datasheet/PCC/53114.pdf.
Supplementary European Search Report dated Feb. 25, 2015, in EP 12824560.2.
Tok et al., "Selection of aptamers for signal transduction proteins by capillary electrophoresis," Electrophoresis, 2010, 31:2055-2062.
Vater et al., "Short bioactive Spiegelmers to migraine-associated calcitonin gene-related peptide rapidly identified by a novel approach: Tailored-SELEX," Nucleic Acids Research, 2003, 31(21):e130.
Wochner et al., "Semi-automated selection of DNA aptamers using magnetic particle handling," BioTechniques, Sep. 1, 2007, 43(3):344-353.
Wurster et al., "Selection and characterization of anti-NF-κB p65 RNA aptamers," RNA, Apr. 22, 2008, 14(6):1037-1047.
Zhao et al., "An RNA aptamer that interfers with the DNA binding of the HSF transcription activator," Nucleic Acids Research, 2006, 34(13):3755-3761.

* cited by examiner

Primary Examiner — Richard A Schnizer
(74) Attorney, Agent, or Firm — Foley & Lardner LLP

(57) ABSTRACT

An object of the present invention is to develop and provide a method for efficiently and conveniently producing a nucleic acid aptamer, particularly, a DNA aptamer, having high specificity for and high binding activity against a target substance.

8 Claims, 11 Drawing Sheets

Fig. 3A  Consensus sequence  5'-AGGGGWWWCAC-3'  (SEQ ID NO: 1)
3'-GTCACWWWGGG-5'  (SEQ ID NO: 2)

Fig. 3B  5R01-derived  5'-AGGGGATTCAC-3'  (SEQ ID NO: 3)
3'-GTCACTAAGGG-5'  (SEQ ID NO: 4)

Fig. 3C  5R14-derived  5'-AGGGGAAACAC-3'  (SEQ ID NO: 5)
3'-GTCACTTTGGG-5'  (SEQ ID NO: 6)

Fig. 3D  5R05-derived  5'-AGGGGTTTCAC-3'  (SEQ ID NO: 7)
3'-GTCACAAAGGG-5'  (SEQ ID NO: 8)

Fig. 4

(SEQ ID NO: 25)   5'-terminal primer-binding region                                   Central region                                3'-terminal primer-binding region

5'-GTAGTCACTAATCCGTTCGAGTCATGC-(N)₄₃-GTGGACTGATACGATCGATTGACAG-3'

| Clone name | (The number of clone) | Sequence |
|---|---|---|
| 5R01 | (23) | CGGGGAATCACTGTAGGGACATTACGCAGGGGATTCACTAGGA (SEQ ID NO:9) |
| 5R09 | (1)  | CGGGGAATCACTGTAGGGACACAATACGCAGGGGATTCACTAGGA (SEQ ID NO:10) |
| 5R43 | (1)  | CGGGGAATCACTGTAGGGACATTACGCAGGGGATTCACTGGGA (SEQ ID NO:11) |
| 5R14 | (3)  | CACGGGGGTTTCACTGTTTCGTAGATTGCATAAGGGAAAACACT (SEQ ID NO:12) |
| 5R13 | (3)  | CACGGGGGTTTCACTGTTTCGTTTCGTAGATTGCATAAGGGAAAACACT (SEQ ID NO:13) |
| 5R34 | (1)  | CACGGGGGTTTCACTGTTTTCGTAGATTGCATAAGGGAAAACACT (SEQ ID NO:14) |
| 5R10 | (1)  | CACGGGGGTTTCACTGTTT-GTAGATTGCATAAGGGAAAACACT (SEQ ID NO:15) |
| 5R26 | (1)  | CACGGGGGTTTCACTGTTTCGTTGATTGCATAAGGGAAAACACT (SEQ ID NO:16) |
| 5R27 | (1)  | CACGGGGGTTTCACTGTTTCGTTGACTGCATAAGGGAAAACACT (SEQ ID NO:17) |
| 5R11 | (1)  | CACGGGGGTTTCACTGTTTTAGTTGATTGCATAAGGGAAAACACT (SEQ ID NO:18) |
| 5R05 | (3)  | TGTAACGTAGGGGTTTCACCAACACTGGGGAAAACACTGAAGC (SEQ ID NO:19) |
| 5R28 | (1)  | TGTAACGTAGGGGTTTCACCATCACTGCGGAAAACACTGAGGC (SEQ ID NO:20) |
| 5R19 | (1)  | TGCAACGTAGGGGTTTCACCAACACTGGGGAAAACACTGAAGC (SEQ ID NO:21) |

■ : 3'-terminal primer-binding region (5'-ctgatacgatcgattgacag)
(Nucleotides 76-95 of SEQ ID NO. 27)

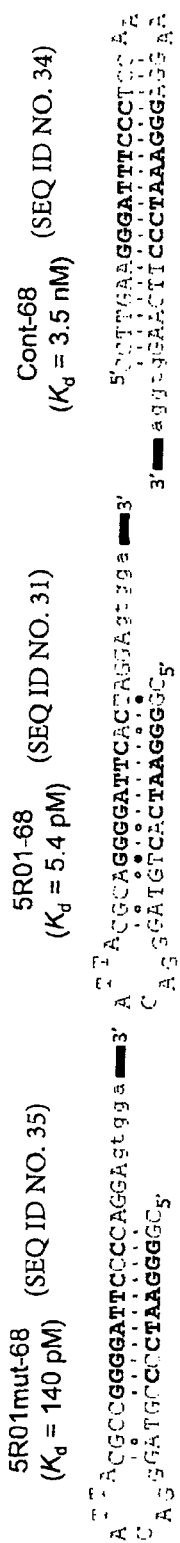

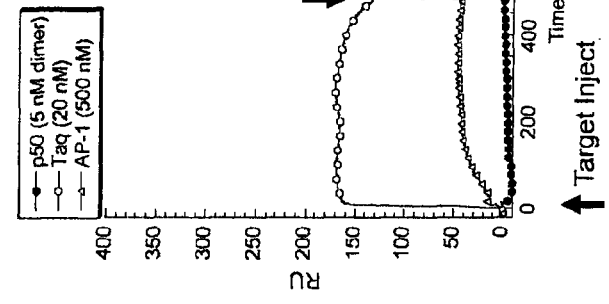
Fig. 11A — 5R01-68 (SEQ ID NO. 31)
Fig. 11B — 5R01mut-68 (SEQ ID NO. 35)
Fig. 11C — Taq-59 (SEQ ID NO. 36)
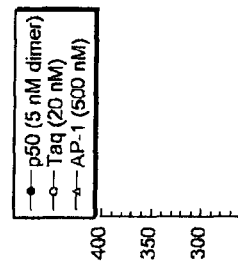
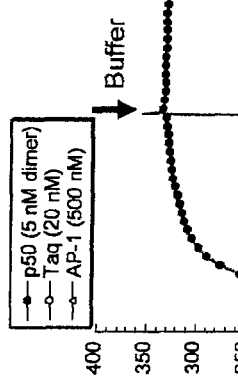
■ : 3'-terminal primer-binding region (5'-ctgatacgatcgattgacag)
(Nucleotides 76-95 of SEQ ID NO. 27)

SEQUENCE LISTING

```
<160> NUMBER OF SEQ ID NOS: 39

<210> SEQ ID NO 1
<211> LENGTH: 11
<212> TYPE: DNA
<213> ORGANISM: Artificial
<220> FEATURE:
<223> OTHER INFORMATION: NFkB p50 binding sequence

<400> SEQUENCE: 1
aggggwwwca c                                                         11

<210> SEQ ID NO 2
<211> LENGTH: 11
<212> TYPE: DNA
<213> ORGANISM: Artificial
<220> FEATURE:
<223> OTHER INFORMATION: NFkB p50 binding sequence
```

<400> SEQUENCE: 2
gggwwwcact g                                                              11

<210> SEQ ID NO 3
<211> LENGTH: 11
<212> TYPE: DNA
<213> ORGANISM: Artificial
<220> FEATURE:
<223> OTHER INFORMATION: NFkB p50 binding sequence

<400> SEQUENCE: 3
aggggattca c                                                              11

<210> SEQ ID NO 4
<211> LENGTH: 11
<212> TYPE: DNA
<213> ORGANISM: Artificial
<220> FEATURE:
<223> OTHER INFORMATION: NFkB p50 binding sequence

<400> SEQUENCE: 4
gggaatcact g                                                              11

<210> SEQ ID NO 5
<211> LENGTH: 11
<212> TYPE: DNA
<213> ORGANISM: Artificial
<220> FEATURE:
<223> OTHER INFORMATION: NFkB p50 binding sequence

<400> SEQUENCE: 5
aggggaaaca c                                                              11

<210> SEQ ID NO 6
<211> LENGTH: 11
<212> TYPE: DNA
<213> ORGANISM: Artificial
<220> FEATURE:
<223> OTHER INFORMATION: NFkB p50 binding sequence

<400> SEQUENCE: 6
gggtttcact g                                                              11

<210> SEQ ID NO 7
<211> LENGTH: 11
<212> TYPE: DNA
<213> ORGANISM: Artificial
<220> FEATURE:
<223> OTHER INFORMATION: NFkB p50 binding sequence

<400> SEQUENCE: 7
aggggtttca c                                                              11

<210> SEQ ID NO 8
<211> LENGTH: 11
<212> TYPE: DNA
<213> ORGANISM: Artificial
<220> FEATURE:
<223> OTHER INFORMATION: NFkB p50 binding sequence

<400> SEQUENCE: 8
gggaaacact g                                                              11

<210> SEQ ID NO 9

<211> LENGTH: 43
<212> TYPE: DNA
<213> ORGANISM: Artificial
<220> FEATURE:
<223> OTHER INFORMATION: middle region of DNA aptamer 5R01

<400> SEQUENCE: 9
cggggaatca ctgtagggac attacgcagg ggattcacta gga                43

<210> SEQ ID NO 10
<211> LENGTH: 43
<212> TYPE: DNA
<213> ORGANISM: Artificial
<220> FEATURE:
<223> OTHER INFORMATION: middle region of DNA aptamer 5R09

<400> SEQUENCE: 10
cggggaatca ctgtagggac aatacgcagg ggattcacta gga                43

<210> SEQ ID NO 11
<211> LENGTH: 43
<212> TYPE: DNA
<213> ORGANISM: Artificial
<220> FEATURE:
<223> OTHER INFORMATION: middle region of DNA aptamer 5R43

<400> SEQUENCE: 11
cggggaatca ctgtagggac attacgcagg ggattcactg gga                43

<210> SEQ ID NO 12
<211> LENGTH: 43
<212> TYPE: DNA
<213> ORGANISM: Artificial
<220> FEATURE:
<223> OTHER INFORMATION: middle region of DNA aptamer 5R14

<400> SEQUENCE: 12
cacggggttt cactgtttcg tagattgcat aagggggaaac act               43

<210> SEQ ID NO 13
<211> LENGTH: 43
<212> TYPE: DNA
<213> ORGANISM: Artificial
<220> FEATURE:
<223> OTHER INFORMATION: middle region of DNA aptamer 5R13

<400> SEQUENCE: 13
cacggggttt cactgtttcg tcgattgcat aaggggaaac act                43

<210> SEQ ID NO 14
<211> LENGTH: 43
<212> TYPE: DNA
<213> ORGANISM: Artificial
<220> FEATURE:
<223> OTHER INFORMATION: middle region of DNA aptamer 5R34

<400> SEQUENCE: 14
cacggggttt cactgttttg tagattgcat aaggggaaac act                43

<210> SEQ ID NO 15
<211> LENGTH: 42
<212> TYPE: DNA
<213> ORGANISM: Artificial
<220> FEATURE:
<223> OTHER INFORMATION: middle region of DNA aptamer 5R10

<400> SEQUENCE: 15
cacggggttt cactgtttgt agattgcata aggggaaaca ct                    42

<210> SEQ ID NO 16
<211> LENGTH: 43
<212> TYPE: DNA
<213> ORGANISM: Artificial
<220> FEATURE:
<223> OTHER INFORMATION: middle region of DNA aptamer 5R26

<400> SEQUENCE: 16
cacggggttt cactgtttcg ttgattgcat aaggggaaac act                   43

<210> SEQ ID NO 17
<211> LENGTH: 43
<212> TYPE: DNA
<213> ORGANISM: Artificial
<220> FEATURE:
<223> OTHER INFORMATION: middle region of DNA aptamer 5R27

<400> SEQUENCE: 17
cacggggttt cactgtttcg ttgactgcat aaggggaaac act                   43

<210> SEQ ID NO 18
<211> LENGTH: 43
<212> TYPE: DNA
<213> ORGANISM: Artificial
<220> FEATURE:
<223> OTHER INFORMATION: middle region of DNA aptamer 5R11

<400> SEQUENCE: 18
cacggggttt cactgtttag ttgattgcat aaggggaaac act                   43

<210> SEQ ID NO 19
<211> LENGTH: 43
<212> TYPE: DNA
<213> ORGANISM: Artificial
<220> FEATURE:
<223> OTHER INFORMATION: middle region of DNA aptamer 5R05

<400> SEQUENCE: 19
tgtaacgtag gggtttcacc aacactgcgg gaaacactga agc                   43

<210> SEQ ID NO 20
<211> LENGTH: 43
<212> TYPE: DNA
<213> ORGANISM: Artificial
<220> FEATURE:
<223> OTHER INFORMATION: middle region of DNA aptamer 5R28

<400> SEQUENCE: 20
tgtaacgtag gggtttcacc atcactgcgg gaaacactga ggc                   43

<210> SEQ ID NO 21
<211> LENGTH: 43
<212> TYPE: DNA
<213> ORGANISM: Artificial
<220> FEATURE:
<223> OTHER INFORMATION: middle region of DNA aptamer 5R19

<400> SEQUENCE: 21
tgcaacgtag gggtttcacc aacactgcgg gaaacactga agc                   43

<210> SEQ ID NO 22
<211> LENGTH: 79
<212> TYPE: DNA

```
<213> ORGANISM: Artificial
<220> FEATURE:
<223> OTHER INFORMATION: DNA library
<220> FEATURE:
<221> NAME/KEY: misc_feature
<222> LOCATION: (19)..(61)
<223> OTHER INFORMATION: n is a, c, g, or t

<400> SEQUENCE: 22
aatccgttcg agtcatgcnn nnnnnnnnnn nnnnnnnnnn nnnnnnnnnn nnnnnnnnnn    60
ncagctggtg atcagatcg                                                 79

<210> SEQ ID NO 23
<211> LENGTH: 19
<212> TYPE: DNA
<213> ORGANISM: Artificial
<220> FEATURE:
<223> OTHER INFORMATION: primer

<400> SEQUENCE: 23
tcgatctgat caccagctg                                                 19

<210> SEQ ID NO 24
<211> LENGTH: 18
<212> TYPE: DNA
<213> ORGANISM: Artificial
<220> FEATURE:
<223> OTHER INFORMATION: primer

<400> SEQUENCE: 24
aatccgttcg agtcatgc                                                  18

<210> SEQ ID NO 25
<211> LENGTH: 95
<212> TYPE: DNA
<213> ORGANISM: Artificial
<220> FEATURE:
<223> OTHER INFORMATION: DNA library
<220> FEATURE:
<221> NAME/KEY: misc_feature
<222> LOCATION: (28)..(70)
<223> OTHER INFORMATION: n is a, c, g, or t

<400> SEQUENCE: 25
gtagtcacta atccgttcga gtcatgcnnn nnnnnnnnn nnnnnnnnnn nnnnnnnnnn      60
nnnnnnnnnn gtggactgat acgatcgatt gacag                               95

<210> SEQ ID NO 26
<211> LENGTH: 26
<212> TYPE: DNA
<213> ORGANISM: Artificial
<220> FEATURE:
<223> OTHER INFORMATION: primer

<400> SEQUENCE: 26
tctgtcaatc gatcgtatca gtccac                                         26

<210> SEQ ID NO 27
<211> LENGTH: 27
<212> TYPE: DNA
<213> ORGANISM: Artificial
<220> FEATURE:
<223> OTHER INFORMATION: primer

<400> SEQUENCE: 27
gtagtcacta atccgttcga gtcatgc                                        27
```

<210> SEQ ID NO 28
<211> LENGTH: 46
<212> TYPE: DNA
<213> ORGANISM: Artificial
<220> FEATURE:
<223> OTHER INFORMATION: NFkB p50 binding sequence

<400> SEQUENCE: 28
tcaagcgaag cttgaaggga tttccctgcg aagcagggaa atccct         46

<210> SEQ ID NO 29
<211> LENGTH: 10
<212> TYPE: DNA
<213> ORGANISM: Artificial
<220> FEATURE:
<223> OTHER INFORMATION: NFkB p50 binding sequence
<220> FEATURE:
<221> NAME/KEY: misc_feature
<222> LOCATION: (4)..(8)
<223> OTHER INFORMATION: r is a or g.  y is c or t.  n is a, c, g, or t.

<400> SEQUENCE: 29 gggrnnyycc         10

<210> SEQ ID NO 30
<211> LENGTH: 21
<212> TYPE: DNA
<213> ORGANISM: Artificial
<220> FEATURE:
<223> OTHER INFORMATION: primer

<400> SEQUENCE: 30
tctgtcaatc gatcgtatca g         21

<210> SEQ ID NO 31
<211> LENGTH: 68
<212> TYPE: DNA
<213> ORGANISM: Artificial
<220> FEATURE:
<223> OTHER INFORMATION: aptamer 5R01-68

<400> SEQUENCE: 31
cggggaatca ctgtagggac attacgcagg ggattcacta ggagtggact gatacgatcg         60
attgacag         68

<210> SEQ ID NO 32
<211> LENGTH: 68
<212> TYPE: DNA
<213> ORGANISM: Artificial
<220> FEATURE:
<223> OTHER INFORMATION: aptamer 5R14-68

<400> SEQUENCE: 32
cacggggttt cactgtttcg tagattgcat aagggaaac actgtggact gatacgatcg         60
attgacag         68

<210> SEQ ID NO 33
<211> LENGTH: 68
<212> TYPE: DNA
<213> ORGANISM: Artificial
<220> FEATURE:
<223> OTHER INFORMATION: aptamer 5R05-68

<400> SEQUENCE: 33

-continued

```
tgtaacgtag gggtttcacc aacactgcgg gaaacactga agcgtggact gatacgatcg      60
attgacag                                                              68
```

<210> SEQ ID NO 34
<211> LENGTH: 68
<212> TYPE: DNA
<213> ORGANISM: Artificial
<220> FEATURE:
<223> OTHER INFORMATION: aptamer Cont-68

<400> SEQUENCE: 34

```
ccttgaaggg atttccctcc aaaaggaggg aaatcccttc aaggtggact gatacgatcg      60
attgacag                                                              68
```

<210> SEQ ID NO 35
<211> LENGTH: 68
<212> TYPE: DNA
<213> ORGANISM: Artificial
<220> FEATURE:
<223> OTHER INFORMATION: aptamer 5R01-68mut

<400> SEQUENCE: 35

```
cggggaatcc ccgtagggac attacgccgg ggattcccca ggagtggact gatacgatcg      60
attgacag                                                              68
```

<210> SEQ ID NO 36
<211> LENGTH: 59
<212> TYPE: DNA
<213> ORGANISM: Artificial
<220> FEATURE:
<223> OTHER INFORMATION: aptamer Taq-59

<400> SEQUENCE: 36

```
aagaccagac aatgtacagt attggcctga aggagtggac tgatacgatc gattgacag       59
```

<210> SEQ ID NO 37
<211> LENGTH: 7
<212> TYPE: DNA
<213> ORGANISM: Artificial
<220> FEATURE:
<223> OTHER INFORMATION: mini-hairpin

<400> SEQUENCE: 37

```
gcgaagc                                                                7
```

<210> SEQ ID NO 38
<211> LENGTH: 10
<212> TYPE: DNA
<213> ORGANISM: Artificial
<220> FEATURE:
<223> OTHER INFORMATION: mini-hairpin

<400> SEQUENCE: 38

```
cgcgaaagcg                                                            10
```

<210> SEQ ID NO 39
<211> LENGTH: 10
<212> TYPE: DNA
<213> ORGANISM: Artificial
<220> FEATURE:
<223> OTHER INFORMATION: NFkB p50 binding sequence
<220> FEATURE:
<221> NAME/KEY: misc_feature
<222> LOCATION: (3)..(7)
<223> OTHER INFORMATION: r is a or g.  y is c or t.  n is a, c, g, or t.

```
<400> SEQUENCE: 39 ccyynnrggg                                                    10
```

METHOD FOR PREPARING NUCLEIC ACID APTAMER

CROSS-REFERENCE TO RELATED APPLICATIONS

This application is a Divisional of U.S. application Ser. No. 14/237,645, which is the U.S. National Stage application of PCT/JP2012/070188, filed Aug. 8, 2012, which claims priority from Japanese application JP 2011-177112, filed Aug. 12, 2011.

The instant application contains a Sequence Listing which has been submitted in ASCII format via EFS-WEB and is hereby incorporated by reference in its entirety. Said ASCII copy, created on Jul. 19, 2017, is named Sequence Listing 07192017.txt and is 8.22 KB.

TECHNICAL FIELD

The present invention relates to a method for efficiently preparing a nucleic acid aptamer, particularly, a DNA aptamer.

BACKGROUND ART

In recent years, nucleic acid aptamers, as with other functional nucleic acids such as siRNAs, have received attention as novel active ingredients for pharmaceutical drugs or diagnostic drugs in place of low-molecular-weight compounds and are under research and development in various ways around the world with the aim of medically applying the aptamers.

These nucleic acid aptamers are functional nucleic acids capable of strongly and specifically binding, through their own conformations, to target substances such as proteins to inhibit or suppress the functions of the target substances. The nucleic acid aptamers are typically produced as nucleic acid molecules binding to target substances from nucleic acid libraries comprising random nucleotide sequences by an in vitro selection method called SELEX (systematic evolution of ligands by exponential enrichment) (Patent Literatures 1 to 3 and Non Patent Literatures 1 to 4).

Conventional nucleic acid aptamers are predominantly RNA aptamers composed of RNAs. The RNAs, however, are unstable and are produced at high cost. For these reasons, research and development have been being shifted in recent years to DNA aptamers, which are stable in vivo and can be inexpensively produced (Patent Literature 4 and Non Patent Literatures 5 to 8). Nevertheless, the DNA aptamers are difficult to produce efficiently, compared with the RNA aptamers. The SELEX method typically involves a method for isolating a complex formed by the binding between the target substance and the nucleic acid aptamer and adopts, as this method, (1) a method which involves trapping proteins onto a nitrocellulose filter through the use of hydrophobic interaction to thereby recover the complex, (2) a method which involves recovering the complex on the basis of mobility shift on a gel during gel electrophoresis, or (3) a method which involves labeling in advance target substances, immobilizing the target substances onto an affinity support or the like on the basis of the labels, and mixing the resulting support with a DNA library.

DNAs, however, are more hydrophobic than RNAs and are therefore nonspecifically adsorbed onto the nitrocellulose filter. In this respect, the method (1) exhibits an undesired high background. The method (2) is unsuitable for the formation of target substance-DNA complexes in large volumes, because possible electrophoresis is limited by gel size. In addition, the DNA library, which consists of plural types of different sequences, tends to produce disturbed electrophoretic bands. Unlike the nitrocellulose filter method, disadvantageously, this method does not permit washing operation of the trapped complex. The method (3) fails to yield aptamers having high binding ability, because DNAs hardly bind to the solid phase-bound surface of the target substances. In addition, DNAs bound both with the target substance and with the solid-phase support are obtained, resulting in undesired high background.

CITATION LIST

Patent Literature

Patent Literature 1: WO1991/019813
Patent Literature 2: WO1994/008050
Patent Literature 3: WO996/040159
Patent Literature 4: WO1992/014843

Non Patent Literature

Non Patent Literature 1: Lauhon C. T. and Szostak J. W., 1995, J. Am. Chem. Soc., 117: 1246-1257
Non Patent Literature 2: Zhao X., et al., 2006, Nucleic Acids Res., 34: 3755-3761
Non Patent Literature 3: Fan X., et al., 2004, J. T. Lis, 101: 6934-6939
Non Patent Literature 4: Jeong S., et al., 2010, Oligonucleotides, 20: 155-161
Non Patent Literature 5: Cho M., et al., Proc. Natl. Acad. Sci. USA, 2010, 107: 15373-15378
Non Patent Literature 6: Tok J., et al., Electrophoresis, 2010, 31: 2055-2062
Non Patent Literature 7: Hamula C. L., et al., 2008, Anal. Chem. 80: 7812-7819
Non Patent Literature 8: Bock L. C., et al., 1992, Nature, 355: 564-566

SUMMARY OF INVENTION

Technical Problem

An object of the present invention is to develop and provide a method for efficiently and conveniently producing a nucleic acid aptamer, particularly, a DNA aptamer, having high specificity for and high binding activity against a target substance.

Another object of the present invention is to provide a nucleic acid molecule that comprises non-Watson-Crick base pairing in a double-stranded region and is capable of specifically and strongly binding to a target substance.

A further object of the present invention is to provide an inhibitor of target substance function comprising the nucleic acid molecule as an active ingredient and a pharmaceutical composition comprising the inhibitor.

Solution to Problem

To attain the objects, the present inventors have modified the SELEX method and consequently successfully developed a novel method for producing a nucleic acid aptamer, which prevents the nonspecific adsorption of DNAs, etc. and can reduce a background. Specifically, the conventional SELEX method adopts a method which involves first coupling a target substance to a solid-phase support, then adding thereto a single-stranded nucleic acid library, and recovering a nucleic acid aptamer bound with the target substance on the solid-phase support. Instead, a target substance is first mixed with a single-stranded nucleic acid library to form a complex of a single-stranded nucleic acid and the target substance. Subsequently, the target substance is immobilized onto a solid-phase support via connector(s) adsorbed on the target substance and/or the solid-phase support. Single-stranded nucleic acids in a free state are washed off. In this way, only the complexed single-stranded nucleic acid was successfully recovered efficiently. This has enabled reduction in background attributed to nonspecific adsorption as well as production of a nucleic acid aptamer very strongly and specifically binding to a target substance. The present invention is based on these development results and provides the following:

(1) A method for producing a nucleic acid aptamer, comprising: a complex formation step of mixing a single-stranded nucleic acid library with a target substance in a solution to form a complex of a single-stranded nucleic acid and the target substance; an immobilization step of mixing the solution after the complex formation step with a solid-phase support to immobilize the complex onto the solid-phase support via connector(s) adsorbed on the target substance and/or the solid-phase support; a recovery step of recovering the complex immobilized on the solid-phase support from the solution; an amplification step of recovering the single-stranded nucleic acid from the complex and then amplifying the single-stranded nucleic acid by a nucleic acid amplification method; and a single-stranded nucleic acid preparation step of converting the double-stranded nucleic acids obtained in the amplification step into single strands and then forming an intramolecular conformation.

(2) The production method according to (1), further comprising a repetitive step of repeating several times the round from the complex formation step to the single-stranded nucleic acid preparation step using the single-stranded nucleic acids obtained in the single-stranded nucleic acid preparation step as a new single-stranded nucleic acid library.

(3) The production method according to (2), wherein the repetitive step involves repeating 2 to 15 times the round from the complex formation step to the single-stranded nucleic acid preparation step.

(4) The production method according to (2) or (3), further comprising a selection step of selecting a single-stranded nucleic acid from among the single-stranded nucleic acids obtained after the repetitive step, wherein the single-stranded nucleic acid comprises in its secondary structure one or more double-stranded regions each consisting of a pair of consecutive 5 to 20 bases base-paired each other and at least one of the double-stranded regions comprises 1 to 10 base pairs consisting of non-Watson-Crick base pairs.

(5) The production method according to any of (1) to (4), wherein in the complex formation step, the solution comprises a competitive substance that competes with the single-stranded nucleic acid for binding with the target substance.

(6) The production method according to any of (1) to (5), wherein the nucleic acid is a DNA.

(7) The production method according to any of (1) to (6), wherein the target substance is a peptide.

(8) The production method according to any of (1) to (7), wherein the connectors are biotin and avidin, streptavidin, or NeutrAvidin.

(9) The production method according to any of (1) to (8), wherein the solid-phase support is hydrophilic.

(10) The production method according to any of (1) to (9), wherein the solution or a buffer used in the complex formation step and/or the recovery step comprises a surfactant.

(11) A nucleic acid molecule binding to a target substance, wherein the nucleic acid molecule comprises one or more double-stranded regions each consisting of a pair of consecutive 5 to 20 bases base-paired each other and at least one of the double-stranded regions comprises 1 to 10 base pairs consisting of non-Watson-Crick base pairs.

(12) The nucleic acid molecule according to (11), wherein the nucleic acid molecule consists of a single-stranded nucleic acid or a double-stranded nucleic acid.

(13) The nucleic acid molecule according to (12), wherein the nucleic acid molecule is a DNA.

(14) The nucleic acid molecule according to any of (11) to (13), wherein the target substance is a peptide.

(15) The nucleic acid molecule according to (14), wherein the peptide is a transcriptional regulator, a signaling factor, a protein ligand, or a receptor protein.

(16) The nucleic acid molecule according to (15), wherein the transcriptional regulator is NF-κB.

(17) The nucleic acid molecule according to (16), wherein the NF-κB is p50, and the nucleic acid molecule comprises a double-stranded region consisting of the nucleotide sequences represented by SEQ ID NOs: 1 and 2.

(18) The nucleic acid molecule according to (17), wherein the nucleic acid molecule comprises a double-stranded region consisting of the nucleotide sequences represented by SEQ ID NOs: 3 and 4, SEQ ID NOs: 5 and 6, or SEQ ID NOs: 7 and 8.

(19) The nucleic acid molecule according to (18), wherein the nucleic acid molecule comprises the nucleotide sequence represented by any of SEQ ID NOs: 9 to 21.

(20) An inhibitor of target substance function comprising a nucleic acid molecule according to any of (11) to (19) as an active ingredient.

(21) A pharmaceutical composition comprising an inhibitor of target substance function according to (20).

(22) A method comprising using a nucleic acid molecule according to any of (11) to (15) to detect a target substance to which the nucleic acid molecule binds, in a sample.

(23) A method comprising detecting NF-κB p50 in a sample using a nucleic acid molecule according to any of (16) to (19).

(24) The method according to (22) or (23), wherein the detection is performed using surface plasmon resonance assay, quartz crystal microbalance assay, turbidimetry, colorimetry, or fluorometry.

(25) A kit for NF-κB p50 detection comprising at least one nucleic acid molecule according to any of (16) to (19).

The present specification encompasses the contents described in the specification and/or drawings of Japanese Patent Application No. 2011-177112 on which the priority of the present application is based.

Advantageous Effects of Invention

The method for producing a nucleic acid aptamer according to the present invention can efficiently and conveniently produce a nucleic acid aptamer, particularly, a DNA aptamer, having high specificity for and high binding activity against a target substance.

The nucleic acid molecule of the present invention comprising non-Watson-Crick base pairing in a double-stranded region can provide a nucleic acid molecule capable of specifically and strongly binding to a target substance.

BRIEF DESCRIPTION OF DRAWINGS

FIGS. 3A-3D show the specific nucleotide sequences of a consensus sequence found in a double-stranded region in the nucleic acid molecule of the present invention whose target substance is NF-κB p50 (FIG. 3A) and consensus sequences found in DNA aptamers obtained by the production method of the present invention (FIGS. 3B to 3D), SEQ ID NO of each strand, and their base pairing. In the nucleotide sequence of the consensus sequence shown in FIG. 3A), the base pair indicated by "W-W" represents "a-t" or "t-a". The symbol "|" between the paired bases in the double-stranded region represents a Watson-Crick base pair. The "open circle" and the "filled circle" between the paired bases represent non-Watson-Crick base pairs consisting of "a-g" or "g-a" and "g-t" or "t-g", respectively.

FIG. 4 shows the nucleotide sequences of NF-κB p50-binding DNA aptamers obtained in the method for producing a nucleic acid aptamer according to the present invention, clone names, the numbers of clones, and SEQ ID NOs of the nucleotide sequences of central regions. The uppermost sequence represents the sequence of a single-stranded nucleic acid library used in the production method. In the nucleotide sequence of each DNA aptamer, a sequence analogous to a natural consensus DNA sequence (SEQ ID NO: 29) to which NF-κB binds is surrounded by a black border. The underline represents a region presumed to form a double-stranded region (stem structure) by intramolecular base pairing. The bold face represents a base mutated in an analogous clone sequence compared with the sequence of 5R01, 5R14, or 5R05. The hyphen (-) represents a single-base deletion mutation.

FIGS. 10A-10C show the nucleotide sequences and secondary structures of a variant 5R01mut-68 (FIG. 10A) and the controls 5R01-68 (FIG. 10B) and Cont-68 (FIG. 10C), a SPR sensorgram of the detected interaction between each of the aptamers and NF-κB p50, and their dissociation constants (Kd) for NF-κB p50.

FIGS. 11A-11C show the nucleotide sequences and secondary structures of 5R01-68 (FIG. 11A), 5R01mut-68 for control (FIG. 11B), and Taq-59 for control (FIG. 11C), and a SPR sensorgram of the detected interaction between each of the aptamers and NF-κB p50, Taq DNA polymerase, or AP-1.

DESCRIPTION OF EMBODIMENTS

1. Definition

Figure 1:
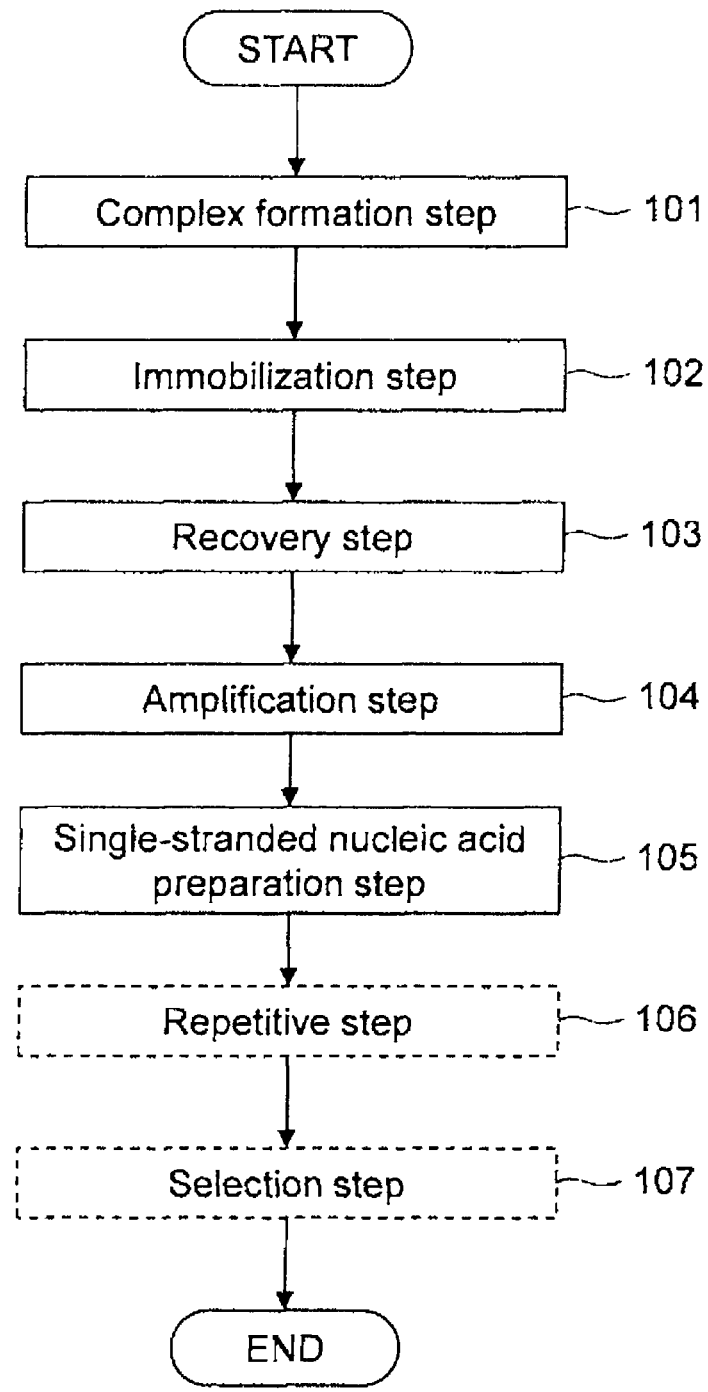
FIG. 1 is a flowchart of steps of the method for producing a nucleic acid aptamer according to the present invention. In the chart, the steps boxed in solid lines represent essential steps, and the steps boxed in broken lines represent optional steps.

The general terms used in the present specification are defined as follows:

In the present specification, the "nucleic acid" or the "nucleic acid molecule" refers to a biological polymer that is constituted by nucleotide units linked through phosphodiester bonds, as a rule. The natural nucleic acid typically corresponds to a naturally occurring or natural nucleic acid such as a DNA consisting of an assembly of deoxyribonucleotides having any of the bases adenine, guanine, cytosine, and thymine, an RNA consisting of an assembly of ribonucleotides having any of the bases adenine, guanine, cytosine, and uracil, or a combination thereof. The nucleic acid of the present invention may partially or wholly comprise a non-natural nucleotide or a non-natural nucleic acid.

In the present specification, the "non-natural nucleotide" refers to an artificially constructed or artificially chemically modified nucleotide and refers to a non-naturally occurring nucleotide similar in properties and/or structure to the natural nucleotide, or a non-naturally occurring nucleotide comprising a nucleoside or a base similar in properties and/or structure to a nucleoside or a base constituting the natural nucleotide. Examples thereof include abasic nucleoside, arabinonucleoside, 2'-deoxyuridine, α-deoxyribonucleoside, β-L-deoxyribonucleoside, and other glycosylated nucleosides. The glycosylated nucleosides include glycosylated nucleosides having substituted pentose (2'-O-methylribose, 2'-deoxy-2'-fluororibose, 3'-O-methylribose, or 1',2'-deoxyribose), arabinose, substituted arabinose sugar, substituted hexose, or an alpha anomer. The none-natural nucleotide of the present invention may be an artificially constructed base analog or an artificially chemically modified base (modified base). Examples of the "base analog" include a 2-oxo(1H)-pyridin-3-yl group, a 5-substituted 2-oxo(1H)-pyridin-3-yl group, a 2-amino-6-(2-thiazolyl)purin-9-yl group, a 2-amino-6-(2-thiazolyl)purin-9-yl group, and a 2-amino-6-(2-oxazolyl)purin-9-yl group. Examples of the "modified base" include modified pyrimidine (e.g., 5-hydroxycytosine, 5-fluorouracil, and 4-thiouracil), modified purine (e.g., 6-methyladenine and 6-thioguanosine), and other heterocyclic bases.

In the present specification, the "non-natural nucleic acid" refers to an artificially constructed nucleic acid analog similar in structure and/or properties to the natural nucleic acid. Examples thereof include a peptide nucleic acid (PNA), a peptide nucleic acid having a phosphate group (PHONA), a bridged nucleic acid or locked nucleic acid (BNA or LNA), and a morpholino nucleic acid. The non-natural nucleic acid can also include chemically modified nucleic acids or nucleic acid analogs such as methylphosphonate-type DNA or RNA, a phosphorothioate-type DNA or RNA, phosphoramidate-type DNA or RNA, and 2'-O-methyl-type DNA or RNA. In the present specification, these non-natural nucleotides and non-natural nucleic acids are collectively referred to as "modified nucleic acids" below for the sake of convenience.

In the present specification, the "nucleic acid aptamer" refers to an aptamer constituted by a nucleic acid and refers to a ligand molecule that is able to strongly and specifically bind to a target substance through the secondary structure of a single-stranded nucleic acid via a hydrogen bond or the like and further the conformation formed on the basis of a tertiary structure, thereby specifically inhibiting or suppressing the functions (e.g., biological activity) of the target substance. The nucleic acid aptamer is generally known as RNA aptamers constituted by RNAs alone and DNA aptamers constituted by DNAs alone. In the present specification, the nucleic acid constituting the nucleic acid aptamer is not particularly limited. The nucleic acid aptamer includes, for example, DNA aptamers, RNA aptamers, aptamers constituted by DNAs and RNAs in combination, aptamers partially comprising modified nucleic acids, and aptamers constituted by modified nucleic acids alone. A DNA aptamer is preferred.

In the present specification, the "target substance" refers to a substance that can serve as a target to which the nucleic acid molecule, particularly, the nucleic acid aptamer binds. The target substance is not particularly limited by its type as long as the target substance is a biomaterial to which the nucleic acid molecule can bind. Examples thereof include peptides (oligopeptides and polypeptides), nucleic acids, lipids, sugars (including sugar chains), and low-molecular-weight compounds. The target substance is preferably a peptide, more preferably a polypeptide, i.e., a protein. The target substance can be appropriately selected according to the purpose. The target substance is usually selected for the purpose of inhibiting, suppressing, or enhancing biological functions unique to the biomaterial. Examples of the unique biological functions include catalytic functions, gene expression control functions (including the control of transcription, translation, transport, etc.), apoptosis control functions, and in a broad sense, the interaction between biomaterials, such as protein-protein interaction responsible for cell signaling. The target substance used may be any of naturally derived substances, chemically synthesized substances, recombinant substances, and the like. A purified single substance that is not contaminated by impurities is preferably used. The polypeptide used as the target substance may be a fusion polypeptide comprising a tag sequence fused therewith. Examples of the tag sequence include hexahistidine (His), FLAG, HA, myc, and GFP.

2. Method for Producing Nucleic Acid Aptamer

2-1. Outline

The first embodiment of the present invention relates to a method for producing a nucleic acid aptamer. The production method of the present invention can reduce a background attributed to the nonspecific adsorption of single-stranded nucleic acids and efficiently and conveniently produce a nucleic acid aptamer, particularly, a DNA aptamer, having high specificity for a target substance.

2-2. Constitution

FIG. 1 shows a flowchart of the steps of the present invention. As shown in this chart, the production method of the present invention comprises a complex formation step (101), an immobilization step (102), a recovery step (103), an amplification step (104), and a single-stranded nucleic acid preparation step (105) as essential steps. Also, the production method of the present invention can comprise a repetitive step (106) and/or a selection step (107) as optional steps, if necessary. Of these steps, the selection step (107) can be performed between the amplification step (104) and the single-stranded nucleic acid preparation step (105) and/or after the repetitive step (106). Hereinafter, each step will be described specifically.

(1) Complex Formation Step

The "complex formation step" (101) is the step of mixing a single-stranded nucleic acid library with a target substance in a solution to form a complex of a single-stranded nucleic acid and the target substance.

In the present invention, the "single-stranded nucleic acid library" refers to a pool constituted by a plurality of identical and/or different single-stranded nucleic acids including candidate molecules of nucleic acid aptamers. The single-stranded nucleic acid library, however, may partially comprise a double-stranded nucleic acid formed by the pairing of all or some bases in a single-stranded nucleic acid with each other. The single-stranded nucleic acid library is, as mentioned above, a library including the nucleic acid aptamer candidates. Each single-stranded nucleic acid constituting the library therefore has a conformation formed by self folding, as a rule.

Figure 2:
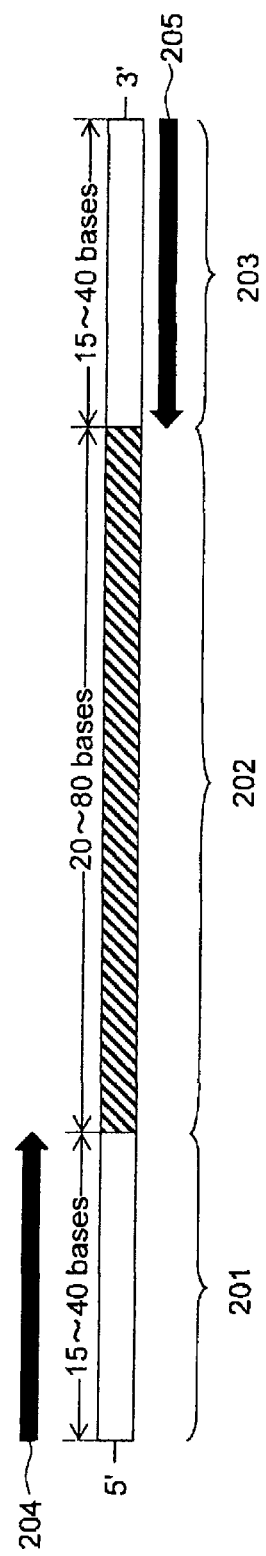
FIG. 2 is a schematic diagram showing the primary structure of each single-stranded nucleic acid constituting a single-stranded nucleic acid library used in the method for producing a nucleic acid aptamer according to the present invention.

The primary structure of each single-stranded nucleic acid constituting the library has, as shown in FIG. 2, 5'-terminal and 3'-terminal primer-binding regions (201 and 203) to which primers bind, and comprises a central region (202) positioned therebetween. The primer regions are each 15 to 40 bases long. The central region is 20 to 80 bases long. Thus, a single-stranded nucleic acid constituting the single-stranded nucleic acid library has a base length ranging from 50 to 160 bases.

The 5'-terminal and 3'-terminal primer-binding regions (201 and 203) have a nucleotide sequence matched to a forward primer (204) and a nucleotide sequence complementary to a reverse primer (205), respectively. It is preferred that: the nucleotide sequence of each primer should be a sequence that does not form a secondary structure in the molecule of the primer and/or a sequence that does not form a consecutive double-stranded region between the forward primer and the reverse primer; each primer should have a Tm value within the range of 50 to 80° C., 55 to 75° C., or 60 to 70° C.; both the primers should not largely differ in Tm value; and each primer should have a GC content of 40 to 60% or 45 to 55%.

The nucleotide sequence of the central region (202) in each single-stranded nucleic acid constituting the single-stranded nucleic acid library consists of a random or particular nucleotide sequence. For use in the first run in the production method of the present invention, the central region desirably has a random sequence, as a rule. The particular nucleotide sequence refers to the nucleotide sequence of a single-stranded nucleic acid placed under a predetermined selective pressure. In this context, the "single-stranded nucleic acid placed under a predetermined selective pressure" corresponds to, for example, a single-stranded nucleic acid constituting a single-stranded nucleic acid library for use in the second run (round 2) or later in the production method of the present invention comprising the repetitive step (106) described later.

The single-stranded nucleic acid library can be appropriately prepared according to a method known in the art. For example, the method of the present invention may be directed to the production of an unknown nucleic acid aptamer capable of binding to a target substance. For this purpose, the single-stranded nucleic acid library for use in the first run is preferably constituted by a population of a large number of different single-stranded nucleic acids. Thus, in this case, the single-stranded nucleic acid library may be prepared by chemical synthesis using, for example, a nucleic acid synthesizer. For example, a single-stranded DNA library can be prepared using a DNA synthesizer. In this case, designed nucleotide sequences can be input into a synthesis program to obtain the library of interest. The synthesis of such nucleotide sequences may be outsourced to each manufacturer to prepare the desired single-stranded nucleic acid library. In the production method of the present invention comprising the repetitive step (106) described later, the single-stranded nucleic acid library for use in round 2 or later can be prepared on the basis of single-stranded nucleic acids obtained in a round immediately before the repetitive step (106).

In the production method of the present invention, the single-stranded nucleic acid library for use in the first run is preferably treated in advance by the intramolecular conformation formation of each single-stranded nucleic acid described in the single-stranded nucleic acid preparation step (105) described later. In order to reduce a single-stranded nucleic acid nonspecifically binding to a solid-phase support for use in the immobilization step (102) described later, the single-stranded nucleic acid library is preferably treated in advance by the removal of a single-stranded nucleic acid nonspecifically binding to the solid-phase support (or each of two or more solid-phase supports used). For this treatment, an appropriate amount of the solid-phase support for use in the immobilization step is added and mixed into a solution containing the single-stranded nucleic acid library. Then, the solid-phase support is removed by recovery, and the resulting solution can be used as the single-stranded nucleic acid library.

In the present invention, the "complex" refers to a nucleic acid-target substance complex that is formed through the binding of each single-stranded nucleic acid constituting the single-stranded nucleic acid library, specifically, a nucleic acid aptamer candidate molecule constituted by the single-stranded nucleic acid, with the target substance.

The solution used in this step is not particularly limited by its type or properties as long as the solution permits formation of the complex between the nucleic acid and the target substance. Water or an aqueous solution is preferred. The aqueous solution can have a pH ranging from 5.0 to 9.0, preferably 6.0 to 8.0, more preferably 6.5 to 7.6. Its salt concentration can be in the range of 20 to 500 mM, preferably 50 to 300 mM, more preferably 90 to 180 mM, in terms of the final concentration. The aqueous solution is preferably a buffer. The buffer is, for example, a pH buffer solution that is applicable to the above pH range (e.g., a phosphate buffer, a citrate-phosphate buffer, a tris-HCl buffer, or a HEPES buffer) and contains an appropriate salt (e.g., NaCl or $CH_3COOK$) added at a final salt concentration within the above range. Specific examples thereof include a PBS buffer (1.1 mM $KH_2PO_4$, 155 mM NaCl, and 3 mM $Na_2HPO_4$, pH 7.4). The composition of the pH buffer can be finely adjusted according to the need on the basis of composition known in the art described in, for example, Sambrook, J. et al., (2001) Molecular Cloning: A Laboratory Manual Third Ed., Cold Spring Harbor Laboratory Press, Cold Spring Harbor, N.Y.

The solution may further contain a reducing agent or a surfactant, if necessary.

Examples of the reducing agent include dithiothreitol (DTT) and 2-mercaptoethanol. The reducing agent in the solution can have a final concentration ranging from 0.5 to 10 mM, preferably 1 to 5 mM.

The surfactant is preferably a nonionic surfactant. Examples thereof include Nonidet P40 (NO-40), Triton X-100, Triton X-114, Brij-35, Brij-58, Tween-20, Tween-40, Tween-60, Tween-80, n-octyl-β-glucoside, MEGA-8, MEGA-9, and MEGA-10. The surfactant in the solution can have a final concentration ranging from 0.005% to 0.1%, preferably 0.01% to 0.08%, in terms of volume/volume (V/V).

The solution used in this step may further contain a competitive substance. In the present specification, the "competitive substance" refers to a substance that competes with the single-stranded nucleic acid for binding with the target substance. The competitive substance is not particularly limited by its type as long as the substance can compete with the single-stranded nucleic acid for binding with the target substance. Examples thereof include nucleic acids, peptides, lipids, sugars, and low-molecular-weight compounds. The competitive substance is preferably a substance similar in properties to the single-stranded nucleic acid serving as the nucleic acid aptamer of interest, for example, a substance binding to the same site on the target substance as that to which the single-stranded nucleic acid binds. Such a substance corresponds to a nucleic acid (single-stranded nucleic acid and/or double-stranded nucleic acid) having a nucleotide sequence analogous to that of the single-stranded nucleic acid of interest. Specifically, when the target substance is, for example, a transcriptional regulator, the competitive substance corresponds to, for example, a nucleotide sequence on the genomic sequence to which the transcriptional regulator originally binds. This nucleic acid used as the competitive substance is designed so as not to have the primer-binding regions (201 and 203) as found in the single-stranded nucleic acid, and the nucleic acid thus prepared can be removed without being amplified in the amplification step (104) described later even if the competitive substance forms a complex with the target substance. The solution containing the competitive substance permits production of a nucleic acid aptamer more strongly binding to the target substance.

In order to form the complex, the single-stranded nucleic acid library and the target substance can be mixed at a ratio of 9:1 to 1:9, preferably 5:5 (volume:volume) and incubated at a temperature ranging from 4 to 40° C., preferably 15 to 37° C., for 5 minutes to 30 minutes or longer, for example, approximately 10 minutes to approximately 1 hour, preferably approximately 20 minutes to approximately 40 minutes.

The formed complex may be washed before the subsequent immobilization step (102). This is because a single-stranded nucleic acid in a free state uncomplexed with the target substance in the solution can be removed or reduced by washing to thereby further reduce a background attributed to the nonspecific binding of the free single-stranded nucleic acid. The washing of the complex can be performed using a method known in the art on the basis of the type of the target substance and the molecular size or characteristics of the complex. When the target substance is, for example, a protein, the complex can be separated from the free single-stranded nucleic acid using an ultrafiltration membrane that permits passage of only a nucleic acid according to molecular size. A buffer for washing may have the same composition as that of the buffer used in the complex formation. The buffer for washing, as with the buffer used in the complex formation, may also contain a reducing agent or a surfactant. The concentration or composition of the reducing agent or the surfactant may be the same as that of the buffer used in the complex formation. Of course, the remaining free single-stranded nucleic acid can also be removed by washing operation in the subsequent immobilization step (102) or the recovery step (103) even if the free single-stranded nucleic acid is not removed or cannot be completely removed at this stage. Thus, the washing may be performed, if necessary.

(2) Immobilization Step

The "immobilization step" (102) is the step of mixing the solution after the preceding step with a solid-phase support to immobilize the complex onto the solid-phase support.

In the present invention, the "solid-phase support" refers to a support in a solid state and includes, for example, magnetic beads, high-molecular-weight polysaccharide supports (e.g., Sepharose, Sephadex, and agarose), silica, glass, metals (e.g., gold, platinum, and silver), plastics, ceramics, resins (natural or synthetic resins), and combinations thereof. The solid-phase support is not limited by its material and preferably has hydrophilic surface for circumventing or reducing the nonspecific binding of, for example, the uncomplexed single-stranded nucleic acid in a free state contained in the solution after the preceding step to the solid-phase support. In this case, the solid-phase support itself may be hydrophilic or may be a hydrophobic support with its surface treated by hydrophilic coating. The support is not particularly limited by its shape. Examples thereof include spherical, nearly spherical, flat, nearly flat, and fiber shapes. Particles having a nearly spherical shape, such as beads, have a large binding surface area and also high operability and as such, are particularly preferred as the shape of the solid-phase support in this step.

In this step, the "immobilization" refers to the coupling of the complex to the solid-phase support. The complex is immobilized onto the solid-phase support via connector(s) adsorbed on the target substance and/or the solid-phase support.

In the present specification, the "connector" refers to a molecule that mediates the coupling of the target substance to the solid-phase support. The connector can include single molecules as well as two or more different molecules linked to each other as long as the connector can mediate the coupling between the target substance and the solid-phase support as a result. Specific examples of such connectors include low-molecular-weight compounds, amino acids, peptides, nucleic acids or their constituents (including nucleosides and nucleotides), and combinations thereof. In this context, the low-molecular-weight compounds refer to natural or chemically synthesized compounds having a molecular weight of approximately hundreds to thousands. Such compounds correspond to, for example, vitamins (including biotin), terpenoids (e.g., carotenoid, heme, and chlorophyll), or polyphenols (e.g., flavonoid, catechin, and tannin). The peptides include antibodies (including recombinant antibodies such as humanized antibodies and multivalent antibodies), or proteins (including enzymes) or their functional fragments. The nucleic acids include DNAs, RNAs, nucleic acid analogs such as locked nucleic acids (LNAs; registered trademark) or peptide nucleic acids (PNAs), or fragments thereof. Examples of the preferred connector(s) according to the present invention include biotin and avidin or streptavidin connectors, lectin-biotin (lectin bound with the biotin) and avidin, streptavidin, or NeutrAvidin connectors, a connector consisting of at least one antibody alone, and connector(s) consisting of an antibody and protein A, G, or L.

The connector(s) is adsorbed on the target substance or the solid-phase support, or both. In this context, the "adsorption" refers to the immobilization of the connector onto the target substance or the solid-phase support through chemical adsorption, physical adsorption, and/or affinity. In this context, the chemical adsorption includes chemical bonds such as covalent bonds, ionic bonds, and hydrogen bonds. The physical adsorption includes coulombic, van der waals, or hydrophobic interaction.

When the connector is adsorbed on only either the target substance or the solid-phase support, this connector is capable of specifically recognizing and binding to a substance of the other side on which the connector is not adsorbed. For example, the connector adsorbed on the solid-phase support specifically recognizes and binds to the target substance. More specifically, when an antibody or an antibody-bound protein A, for example, is adsorbed as the connector on the solid-phase support, the antibody specifically recognizes and binds to the target substance. Hence, the target substance and the solid-phase support are mixed in a solution to thereby couple the target substance to the solid-phase support via the connector. Some or all target substances after the complex formation step (101) have been complexed with single-stranded nucleic acids as nucleic acid aptamer candidates. Thus, this step can immobilize the complex onto the solid-phase support.

When the connector is adsorbed on each of the target substance and the solid-phase support, their connectors (hereinafter, the connector adsorbed on the target substance is referred to as a "first connector", while the connector adsorbed on the solid-phase support is referred to as a "second connector", for the sake of convenience) are capable of specifically binding to each other. For example, biotin may be adsorbed as the first connector on the target substance, while avidin, streptavidin, or NeutrAvidin may be adsorbed as the second connector on the solid-phase support. In this case, the target substance and the solid-phase support are mixed in a solution to thereby allow biotin and avidin, streptavidin, or NeutrAvidin to specifically bind to each other. As a result, the target substance is coupled to the solid-phase support via the binding between biotin and avidin, streptavidin, or NeutrAvidin. Alternatively, an anti-target substance mouse monoclonal IgG antibody may be adsorbed as the first connector on the target substance, while a rabbit anti-mouse IgG antibody or protein A may be adsorbed as the second connector on the solid-phase support. In this case, the target substance and the solid-phase support are mixed in a solution to thereby allow the anti-target substance mouse monoclonal IgG antibody and the rabbit anti-mouse IgG antibody or protein A to specifically bind to each other. As a result, the target substance is coupled to the solid-phase support via the antibody-antibody or antibody-protein A binding. As a result, the complex can be immobilized onto the solid-phase support.

In this step, the target substance in the complex directly contributes to the immobilization of the complex onto the solid-phase support via the connector. Thus, not only the complex but also an uncomplexed target substance in a free state can be immobilized onto the solid-phase support in this step. However, even the immobilization of such a target substance in a free state carrying no single-stranded nucleic acid onto the solid-phase support has no or very slight influence on reduction in the nonspecific adsorption of single-stranded nucleic acids, which is one object of the present invention. Thus, this does not become a particular hindrance to the achievement of the present invention.

The connector can be adsorbed onto the target substance or the solid-phase support by a method differing depending on the types of the target substance, the solid-phase support, and/or the connector. Thus, the connector can be appropriately adsorbed by a method known in the art according to their types or the purpose. For the adsorption of the connector onto the target substance, however, it is desirable that the connector and/or the adsorption method should neither inhibit nor dissociate the binding between the single-stranded nucleic acid and the target substance in the complex. The adsorption of the connector onto any of the target substance and the solid-phase support is preferably carried out by a method that prevents the complex from being easily dissociated due to operation in this step and the subsequent recovery step (103).

When the target substance or the solid-phase support has a functional group, an exemplary adsorption method can involve, for example, using a connector having an active functional group (e.g., an aldehyde group, a carboxyl group, a sulfo group, an amino group, a thiol group, a cyano group, or a nitro group) capable of covalently binding to the functional group or a connector having such an active functional group introduced therein to adsorb the connector onto the target substance or the solid-phase support via a covalent bond formed through chemical reaction such as nucleophilic addition reaction, nucleophilic substitution reaction, or electrophilic substitution reaction between both the functional groups. The combination of such functional groups capable of covalently binding to each other is, for example, an amino group and an aldehyde group, an amino group and an ester group, a thiol group and a maleimide group, an azide group and an acetylene group, an azide group and an amino group, a hydrazine group and a ketone group, or a hydrazine group and an aldehyde group. The method for allowing these functional groups to covalently bind to each other through chemical reaction is a technique well known in the art. In the case of adsorbing, for example, a target protein, onto a biotin connector, an active ester group is introduced to biotin using N-hydroxysuccinimide ester (NHS) or the like. Then, an amide bond can be formed between an amino group in the protein and the ester group to thereby adsorb the protein onto the biotin. Various biotinylating reagents are commercially available from each manufacturer and may be used for adsorbing biotin onto the target substance.

When the target substance is an antigen and the first connector is an antibody specifically recognizing and binding to an epitope in the antigen, the antigen and the antibody can be contacted with each other in an appropriate solution to thereby adsorb the first connector onto the target substance through affinity binding. When the target substance is, for example, a polypeptide, an antibody, if any, capable of specifically recognizing the polypeptide can be adsorbed as the first connector onto the polypeptide. Even in the absence of such an antibody capable of specifically recognizing the polypeptide used as the target substance, an antibody capable of specifically recognizing a tag sequence can be adsorbed as the first connector onto the polypeptide, provided that a fusion polypeptide of the polypeptide and the tag sequence can be synthesized.

The timing of adsorption of the connector is not limited. The adsorption of the connector onto the target substance is preferably carried out after the complex formation step (101) and before this step. This is because the adsorption of the connector onto the target substance before the complex formation step (101) might suppress or inhibit the binding between the target substance and the single-stranded nucleic acid. Thus, the connector is adsorbed onto the target substance at an appropriate time after the complex formation step (101) and before this step and can be adsorbed onto the target substance by any of the adsorption methods described above using, for example, the complex-containing solution obtained after the complex formation step (101). Alternatively, the adsorption of the connector onto the solid-phase support is preferably carried out at least before the mixing of the complex-containing solution with the solid-phase support in this step. This is because use of the connector-adsorbed solid-phase support permits more secure immobilization of the target substance onto the solid-phase support. Thus, the connector can be adsorbed onto the solid-phase support by any of the adsorption methods at least before the mixing of the complex-containing solution with the solid-phase support in this step. Specifically, in the case of adsorbing, for example, biotin as the first connector onto a protein as the target substance and streptavidin as the second connector onto magnetic beads as the solid-phase support, biotin can be adsorbed onto the protein using, for example, a commercially available biotinylating reagent according to the protocol attached thereto and also using the complex-containing solution obtained after the complex formation step (101). Then, unadsorbed biotin is preferably washed off by a method known in the art, for example, ultrafiltration. Also, streptavidin can be adsorbed onto the magnetic beads in advance using a method known in the art, independently of the complex formation step (101). For example, magnetic beads having a tosyl group or an epoxy group can be merely mixed with streptavidin to thereby directly adsorb the streptavidin thereon via the covalent bond between the group and the primary amino group in the streptavidin. Alternatively, magnetic beads having a carboxyl group can be activated by carbodiimide to thereby adsorb the streptavidin thereon via the covalent bond between the activated carboxyl group and the primary amino group in the streptavidin. These methods are well known in the art. Commercially available streptavidin-adsorbed magnetic beads may be purchased and used in the present invention.

Plural types of connectors may be subjected to the immobilization of the target substance onto the solid-phase support. For example, a plurality of different first connectors may be adsorbed onto the target substance. Specific examples of such a case include the adsorption of biotin and an anti-target substance antibody as independent first connectors onto one target substance. In this case, the first connectors are preferably selected so that their respective recognition sites and/or adsorption sites on the target substance do not overlap with each other and/or do not compete with each other. The immobilization step (102) and the recovery step (103) described later are carried out using different solid-phase supports on which second connectors appropriate for these first connectors are respectively adsorbed. As a result, the background of a contaminating single-stranded nucleic acid attributed to nonspecific adsorption on the solid-phase support can be further reduced. Specific examples of such an approach include a method which involves: performing the immobilization step (102) and the recovery step (103) using the target substance with biotin and the anti-target substance antibody adsorbed thereon as the first connectors and the magnetic beads (solid-phase support) with streptavidin adsorbed thereon as the second connector; and then performing again the immobilization step (102) and the recovery step (103) using Sepharose beads as another solid-phase support with protein G adsorbed thereon as the second connector.

In this step, the complex as well as a target substance in a free state uncomplexed with the single-stranded nucleic acid is immobilized onto the solid-phase support. Such an uncomplexed target substance, however, is not problematic because the uncomplexed target substance is also removed in the amplification step (104) described later which involves recovering the single-stranded nucleic acid by the removal of the target substance from the complex.

(3) Recovery Step

The "recovery step" (103) is the step of recovering the complex immobilized on the solid-phase support from the solution.

As mentioned above, the complex is immobilized on via the connector(s) on the solid-phase support after the immobilization step (102). A feature of this step is to separate and recover this complex-immobilized solid-phase support from the solution on the basis of the characteristics of the solid-phase support. The characteristics of the solid-phase support refer to properties unique to the solid-phase support. The characteristics include, for example, magnetic force, specific gravity, fluorescence, luminescence, and affinity.

Specifically, when the solid-phase support is, for example, magnetic beads, the complex-immobilized solid-phase support is recovered using a magnet from the solution after the immobilization step (102) and then washed with a buffer to wash off target substances or single-stranded nucleic acids nonspecifically adsorbed on the solid-phase support. In this way, the complex-immobilized solid-phase support can be recovered. Alternatively, when the solid-phase support is a high-molecular-weight polysaccharide support, silica, a metal (including magnetic beads), or glass, the complex-immobilized solid-phase support is precipitated by centrifugation. After removal of the supernatant, the precipitates can also be washed with a buffer to thereby recover the complex-immobilized solid-phase support. When the solid-phase support is, for example, a high-molecular-weight polysaccharide support carrying a fluorescent material, the complex-immobilized solid-phase support can be recovered using a fluorescence detector such as FACS. Each specific selection method is not particularly limited and can be appropriately determined on the basis of the characteristics of the solid-phase support using a technique known in the art.

The buffer for use in washing in this step can have the same composition as that of the buffer used in the complex formation step (101). The buffer may further contain a reducing agent or a surfactant, if necessary. Examples of the reducing agent used include dithiothreitol (DTT) and 2-mercaptoethanol. The reducing agent in the buffer can have a final concentration ranging from 0.5 to 10 mM or 1 to 5 mM. The surfactant is preferably a nonionic surfactant. The surfactant is preferably, for example, Nonidet P40 (NO-40), Triton X-100, Triton X-114, Brij-35, Brij-58, Tween-20, Tween-40, Tween-60, Tween-80, n-octyl-β-glucoside, MEGA-8, MEGA-9, or MEGA-10. The surfactant in the buffer can have a final concentration ranging from 0.005% to 0.1% or 0.01% to 0.08% in terms of volume/volume (V/V).

The washing can be performed one to several times using the buffer and is preferably performed 2 to 3 times. The washing temperature and the washing time are not particularly limited and can be 15 to 50° C. or 20 to 40° C. for 10 minutes to 1 hour.

(4) Amplification Step

The "amplification step" (104) is the step of recovering the single-stranded nucleic acid from the complex, followed by amplification by a nucleic acid amplification method.

In this step, the complex is first eluted, if necessary, from the complex-immobilized solid-phase support recovered in the recovery step (103). The elution method differs depending on the type of the connector(s). When the connector is, for example, an antibody, the complex-immobilized solid-phase support can be dissociated by acid treatment or the like and then neutralized, if necessary, by the addition of an alkali to thereby elute the complex from the complex-immobilized solid-phase support. Alternatively, when the connectors are biotin and avidin, streptavidin, or NeutrAvidin, the complex-immobilized solid-phase support can be heat-treated in a solution containing 7 M or higher urea and/or 2 M or higher β-mercaptoethanol to dissociate the binding between biotin and avidin, streptavidin, or NeutrAvidin and thereby elute the complex therefrom. When the target substance is a glycosylated substance and the connector is lectin, the complex can be eluted by the addition of a sugar such as glucose. These methods can be appropriately performed according to a method known in the art.

The single-stranded nucleic acid can be recovered from the complex by a method differing depending on the type of the target substance complexed therewith. Thus, this recovery can be performed according to a method known in the art for recovering a nucleic acid from a complex consisting of the target substance and the nucleic acid. When the target substance is, for example, a peptide such as a protein, the single-stranded nucleic acid of interest can be recovered by the clotting and removal of the protein according to a protein denaturation method such as an alkali method or a phenol/chloroform method. Alternatively, when the target substance is a lipid or a low-molecular-weight compound, for example, an elution buffer is added to the complex, which is then heat-treated to disrupt the double-stranded structure of the nucleic acid or heat-treated with the elution buffer supplemented with a chelating agent or with the elution buffer pH shifted to that of a binding buffer to disrupt the double-stranded structure of the nucleic acid. The single-stranded nucleic acid thus obtained by the dissociation of the binding between the target substance and the nucleic acid can be recovered by an alcohol precipitation method or the like. Alternatively, a linker that is cleavable using light irradiation, a reducing agent, or the like may be added into a connector for the immobilization of the target substance onto the solid-phase support via the connector. The target substance-bound nucleic acid is cleaved at the linker from the solid-phase support. The nucleic acid molecule can be recovered by an alcohol precipitation method or the like according to the operation mentioned above. Also, the uncomplexed target substance immobilized together with the complex on the solid-phase support in the immobilization step (102) can be removed by this step, as mentioned above.

Subsequently, the single-stranded nucleic acid thus recovered is amplified by a nucleic acid amplification method known in the art. The "nucleic acid amplification method" refers to a method by which a particular region in a template nucleic acid is amplified using primers and an enzyme such as polymerase. The nucleic acid amplification method used in this step can be any method known in the art. Examples thereof include polymerase chain reaction (PCR) and isothermal and chimeric primer-initiated amplification of nucleic acids (ICAN). PCR is preferred.

The polymerase for use in the reaction is appropriately determined depending on the nucleic acid amplification method used. Usually, DNA polymerase, particularly, thermostable DNA polymerase, is used. Such thermostable nucleic acid polymerase is commercially available as various types from each manufacturer such as Takara Bio Inc., New England Biolabs Inc., F. Hoffmann-La Roche Ltd., or Promega Corp. and may be used in the present invention. Polymerase having high fidelity is generally preferred for use in the nucleic acid amplification method. The polymerase used in this step, however, is not necessarily required to have high fidelity and may be polymerase to which an error may be introduced occasionally, such as Taq polymerase.

The reaction conditions of the nucleic acid amplification method can be determined in consideration of the length of a nucleotide sequence to be amplified, the amount of the nucleic acid for template, i.e., the recovered single-stranded nucleic acid, the Tm values of the primers, the optimum reaction temperature and optimum pH of the polymerase used, etc. For example, for PCR, a sequence matched to the 5'-terminal primer-binding region (201) constituting each single-stranded nucleic acid in the single-stranded nucleic acid library is used as the forward primer (204), while a sequence complementary to the 3'-terminal primer-binding region (203) is used as the reverse primer (205). In this case, the reverse primer labeled with a label is convenient because a double-stranded nucleic acid can be selectively separated and purified as each amplification product on the basis of the label from the reaction solution after the amplification reaction and another single-stranded nucleic acid complementary to the single-stranded nucleic acid of interest in the double-stranded nucleic acid can then be separated and removed on the basis of the label. In the case of using commercially available polymerase, a salt ($MgCl_2$, etc.) and dNTPs (N=A, G, C, or T) can be added at appropriate concentrations to a buffer attached thereto to prepare a reaction solution. For PCR involving 3 steps (denaturation, annealing, and extension), the temperature and reaction time of each step are, for example, 90° C. to 98° C. for approximately 30 seconds to approximately 1 minute for the thermal denaturation step, 50° C. to 60° C. for approximately 30 seconds to approximately 1 minute for the annealing step, and 70° C. to 75° C. for approximately 40 seconds to approximately 2 minutes for the extension step. The number of cycles can usually be 10 cycles to 40 cycles. 15 cycles to 20 cycles are preferred.

After the completion of this step and before the single-stranded nucleic acid preparation step, the obtained amplified nucleic acids may be purified, if necessary. This purification can remove unreacted deoxynucleotides and primers or polymerase or the like. The purification method may be any method known in the art. Examples thereof include an ethanol precipitation method and a purification method using a spin-type gel filtration column. The latter method is preferred because the method permits rapid and convenient nucleic acid purification. Such a column is commercially available from each bio-related company and may be used in the present invention.

(5) Single-Stranded Nucleic Acid Preparation Step

The "single-stranded nucleic acid preparation step" (105) is the step of converting the double-stranded nucleic acids obtained in the amplification step (104) into single strands.

Usually, each nucleic acid after the amplification step (104) is not a nucleic acid aptamer consisting of a single-stranded nucleic acid specifically binding to the target substance, but is found as a double-stranded nucleic acid comprising the single-stranded nucleic acid of interest base-paired with another single-stranded nucleic acid having a nucleotide sequence complementary thereto. Thus, in this step, the double-stranded nucleic acid is prepared into single strands. Then, an intramolecular conformation is formed in the single-stranded nucleic acid of interest to prepare a nucleic acid aptamer.

Each double-stranded nucleic acid is generally made into single strands by thermal denaturation. The thermal denaturation can be performed at a temperature ranging from 60 to 90° C. The solution for use in this denaturation may contain 1 to 7 M urea. Then, electrophoresis is performed using a denaturing gel. A band having the size of interest is eluted from the gel to purify the single strand. Such a method known in the art or a method equivalent thereto can achieve the preparation of single strands from double strands and the purification thereof.

The single-stranded nucleic acids prepared in this step are a mixture of nucleic acids capable of forming the nucleic acid aptamer of interest and their partners having a nucleotide sequence complementary to the single-stranded nucleic acid of interest. In this step, such single-stranded nucleic acids having a complementary nucleotide sequence may be removed from the nucleic acids thus single-stranded before formation of the intramolecular conformation to isolate the single-stranded nucleic acids capable of forming the nucleic acid aptamer of interest. Such isolation of the single-stranded nucleic acids having the nucleotide sequence of interest can be achieved by use of, for example, the reverse primer labeled with a label as mentioned above. Use of this method also permits selective separation and purification of the double-stranded nucleic acid as each amplification product on the basis of the label from the reaction solution after the amplification reaction. Specific examples of such a reverse primer that may be used include a biotin-labeled reverse primer. After PCR, each amplified double-stranded nucleic acid in the reaction solution is recovered by an ethanol precipitation method or the like. Then, streptavidin is added to the suspension to form a biotin-streptavidin complex through which the double-stranded nucleic acid is then separated and purified. Then, the purified double-stranded nucleic acid is denatured into single strands, which are in turn fractionated by denaturing gel electrophoresis depending on the difference in mobility between the strands. The single-stranded nucleic acid of interest can be isolated and purified from the gel.

In order to form the intramolecular conformation in each single-stranded nucleic acid thus prepared, for example, the single-stranded nucleic acid can be subjected to heating-cooling treatment. As a specific example, the single-stranded nucleic acid can be dissolved in the buffer (e.g., PBS buffer) used in the complex formation step (101), then thermally denatured at 80 to 98° C., preferably 85 to 95° C., for 30 seconds to 5 minutes, preferably 30 seconds to 3 minutes, and then left, for example, at room temperature for slow cooling or cooled in stages to form the intramolecular conformation. The cooling in stages can be performed, for example, temporal cooling at 50 to 70° C. for approximately 1 minute to approximately 20 minutes after thermal denaturation and then further cooling with the temperature decreased to 15 to 35° C.

This step can produce a nucleic acid aptamer specifically binding to the target substance. The nucleotide sequence of the obtained nucleic acid aptamer can be identified using an ordinary nucleic acid cloning technique known in the art.

For example, the obtained nucleic acid aptamer can be denatured into a linear shape, then inserted into an appropriate cloning vector, and then sequenced through cycle sequencing reaction or the like. These methods are known in the art and can be carried out, for example, using a commercially available kit such as Big Dye Terminator Cycle Sequencing Kit (Life Technologies Corp.) and a sequencer.

(6) Repetitive Step

The "repetitive step" (106) is the step of repeating several times the procedures from the complex formation step (101) to the single-stranded nucleic acid preparation step (105) (hereinafter, this series of steps is referred to as a "round" in the present specification).

This step is an optional step, as mentioned above. Two or more rounds of this repetitive step, however, are preferably performed for narrowing down a nucleic acid aptamer having higher specificity for the target substance after the single-stranded nucleic acid preparation step (105). Specifically, for example, 2 to 15 rounds, 2 to 8 rounds, or 2 to 5 rounds are performed.

In each round (except for the first round), a pool of the single-stranded nucleic acids obtained in the single-stranded nucleic acid preparation step (105) of the immediately preceding round is used as a new single-stranded nucleic acid library for use in the complex formation step (101), as a rule. The library for use in the first round is preferably constituted, as mentioned above, by a population of a large number of different single-stranded nucleic acids and is therefore, desirably, a single-stranded nucleic acid library prepared by chemical synthesis, as a rule. These single-stranded nucleic acid libraries for use in the rounds may be placed under the same or different conditions of the individual steps, i.e., the complex formation step (101) to the single-stranded nucleic acid preparation step (105), among the rounds according to the need. Examples of the different conditions among the rounds include change in the composition of the solution or the buffer used in each round. Specifically, in the early rounds, a larger number of nucleic acid aptamer candidates are acquired under mild washing conditions using the buffer. In the later rounds, a single-stranded nucleic acid more strongly binding to the target substance can be isolated under strict washing conditions using the buffer mixed with approximately 3 M urea. Alternatively, the concentrations of the target substance and the single-stranded nucleic acid library in the complex formation step (101) may be changed among the rounds. For example, the concentrations of the target substance and the single-stranded nucleic acid library can be decreased with each round to render complex formation conditions stricter. As a result, the single-stranded nucleic acid more strongly binding to the target substance can be isolated.

(7) Selection Step

The "selection step" (107) is the step of selecting a single-stranded nucleic acid molecule having a predetermined structure from among the single-stranded nucleic acids obtained after the repetitive step (106). This step is an optional step and can be selectively performed for the purpose of producing a nucleic acid aptamer more strongly binding to the target substance as described later.

In this context, the predetermined structure refers to a secondary structure formed by the single-stranded nucleic acid molecule as the nucleic acid aptamer, wherein the predicted secondary structure comprises one or more double-stranded regions and comprises non-Watson-Crick base pairs in at least one of the double-stranded regions.

The present inventors have found that the nucleic acid aptamer obtained by the production method of the present invention very strongly binds to the target substance when having non-Watson-Crick base pairs in at least one of the double-stranded regions predicted as a target substance-binding region. This step is based on this finding.

In this step, each single-stranded nucleic acid obtained after the repetitive step (106), i.e., after the single-stranded nucleic acid preparation step (105) as the final step in the final round, is sequenced using the method described above in the single-stranded nucleic acid preparation step (105). The secondary structure is predicted on the basis of the determined nucleotide sequence using software such as M-fold (mfold.rna.albany.edu/?q=mfold/). From among the single-stranded nucleic acids thus obtained, a single-stranded nucleic acid sequence is selected which comprises in its secondary structure one or more double-stranded regions (i.e., stem regions) each consisting of a pair of consecutive 5 to 20 bases, 7 to 18 bases, 8 to 17 bases, or 10 to 15 bases base-paired with each other and at least one of the double-stranded regions comprises 1 to 5 base pairs, 1 to 7 base pairs, 1 to 8 base pairs, or 1 to 10 base pairs consisting of non-Watson-Crick base pairs.

In the present specification, the "non-Watson-Crick base pairs" refer to base pairs of guanine (g), adenine (a), cytosine (c), thymine (t), and uracil (u) except for guanine and cytosine (g-c) or adenine and thymine (a-t) or uracil (a-u). The non-Watson-Crick base pairs also include base pairs having a hydrogen bonding pattern different from that of base pairs formed in common double-stranded DNAs (Nagaswamy U., et al., Nucl. Acid Res. 2000, 28: 375-376). Base pairs consisting of, for example, guanine and adenine (g-a) or thymine (g-t), guanine and guanine (g-g), or adenine and adenine (a-a) are preferred.

This step can be performed after the completion of the final round and may be performed after each round and before the start of the next round. In the latter case, the single-stranded nucleic acids having the predetermined structure, obtained in this step, can be used as a single-stranded nucleic acid library in the next round to render the conditions of the individual steps stricter in one round. The nucleic acid aptamer thus produced is capable of further strongly binding to the target substance.

2-3. Effect

The production method of the present invention can efficiently produce a nucleic acid aptamer, particularly, a DNA aptamer, having higher specificity and binding ability at least 100 to 1000 times stronger than those brought about by a conventional method for producing a nucleic acid aptamer, particularly, a DNA aptamer.

3. Nucleic acid molecule

The second embodiment of the present invention relates to a nucleic acid molecule binding to a target substance.

3-1. Constitution

The nucleic acid molecule of the present invention intramolecularly comprises one or more double-stranded regions and comprises non-Watson-Crick base pairs in at least one of the double-stranded regions.

The nucleic acid molecule of the present invention corresponds to, as described above in the paragraph "1. Definition", a natural nucleic acid such as a DNA, an RNA, or a combination thereof, as a rule. Also, the nucleic acid of the present invention may partially or wholly comprise a non-natural nucleotide or a non-natural nucleic acid. The preferred form of the nucleic acid of the present invention is a DNA.

The "double-stranded region" refers to a region formed by consecutive base pairs between the nucleotide strands constituting the nucleic acid molecule. The length of the consecutive base pairs is 5 to 20 bp, 7 to 18 bp, 8 to 17 bp, or 10 to 15 bp. The nucleic acid molecule of the present invention may comprise two or more double-stranded regions. In such a case, each double-stranded region is constituted by base pairs that are the same or different between or among the double-stranded regions. The double-stranded regions constituted by different base pairs may have the same or different lengths. Each double-stranded region may be interrupted by a region (including e.g., mismatch sites, gaps, bulge structures, and internal loop structures) that is not base-paired between the strands. Alternatively, each double-stranded region may be continuous.

The "non-Watson-Crick base pairs" refer to, as mentioned above, base pairs of guanine, adenine, cytosine, thymine, and uracil except for guanine and cytosine or adenine and thymine or uracil. Base pairs consisting of, for example, guanine and adenine or thymine, guanine and guanine (g-g), or adenine and adenine (a-a) are preferred.

The non-Watson-Crick base pairs can be contained in at least one of these double-stranded regions present in the nucleic acid molecule of the present invention. The non-Watson-Crick base pairs contained in one double-stranded nucleic acid region are 1 to 5 base pairs, 1 to 7 base pairs, 1 to 8 base pairs, or 1 to 10 base pairs. The non-Watson-Crick base pairs in one double-stranded nucleic acid region are not particularly limited by their positions.

In the nucleic acid molecule of the present invention, the double-stranded region comprising non-Watson-Crick base pairs is directly involved in binding with the target substance. Thus, its nucleotide sequence differs depending on the type of the target substance. The nucleotide sequence can be a nucleotide sequence that is based on the nucleotide sequence of a double-stranded region already known to bind to the target substance and has the non-Watson-Crick base pairs introduced in a portion thereof. For example, the nucleic acid molecule of the present invention binding to a particular target substance can be based on the nucleotide sequences of a double-stranded region predicted as a target substance-binding site in a decoy DNA, an RNA aptamer, or a DNA aptamer known in the art to bind to the target substance, and can be produced by the introduction of non-Watson-Crick base pairs into both the strands.

The nucleic acid molecule of the present invention binds to a target substance. The "target substance" refers to, as described above in the paragraph "1. Definition", a biomaterial that can serve as a target to which the nucleic acid molecule binds. The target substance is not particularly limited by its type. Examples thereof include peptides, nucleic acids, lipids, sugars, and low-molecular-weight compounds. The target substance is preferably a peptide, more preferably a polypeptide, i.e., a protein. The target substance of the nucleic acid molecule of the present invention is particularly preferably a transcriptional regulator, a signaling factor, a protein ligand (including cytokines and chemokines), or a receptor protein binding to a nucleic acid having a particular nucleotide sequence.

Specific examples of the transcriptional regulator include NF-κB, SP1, E2F, AP-1, and STAT-1.

Specific examples of the signaling factor include Raf, cytohesin 1, phospholipase $A_2$, and HER3.

Specific examples of the protein ligand include VEGF, EGF, NGF, HGF, KGF, bFGF, PDGF, IL-2, -3, -6, -8, -10, or -20, IFN-α, -β, or -γ, TGF-β, BMP, Activin, TNF-α, Wnt, and RANKL.

The nucleic acid molecule of the present invention can bind to the target substance, thereby inhibiting, suppressing, or enhancing biological functions unique to the target substance. The nucleic acid molecule of the present invention usually has a function inhibitory or suppressive effect.

The nucleic acid molecule of the present invention consists of a double-stranded nucleic acid and/or a single-stranded nucleic acid. Hereinafter, the double-stranded nucleic acid and single-stranded nucleic acid fragments will each be described specifically.

<Double-Stranded Nucleic Acid>

The length of each nucleotide strand in the nucleic acid molecule consisting of the double-stranded nucleic acid is not limited and preferably ranges from, for example, 5 to 50 mer, 7 to 40 mer, or 10 to 35 mer. The base-paired strands do not have to have the same lengths. Examples of such a double-stranded nucleic acid include a molecule having one nucleotide strand at least 7 mer longer than the other nucleotide strand. In this case, the longer nucleotide strand may form a hairpin structure through intramolecular annealing in a single-stranded region that is not matched to the other nucleotide strand. A stem region formed in this hairpin structure is also encompassed in the double-stranded region of the present invention.

Each nucleotide strand constituting the double-stranded nucleic acid can contain a single-stranded region that is not base-paired with the other strand, at the 5' end and/or 3' end of the double-stranded region. The double-stranded nucleic acid also encompasses a dumbbell-shaped nucleic acid in a closed ring form in which both the nucleotide strands of the double-stranded nucleic acid are linked via loop structures formed by these single-stranded regions as in linker nucleic acids. Such a dumbbell-shaped nucleic acid is preferred as the nucleic acid molecule of the present invention because of its resistance to degradation by a nucleolytic enzyme such as nuclease, compared with the linear double-stranded nucleic acid.

Either or both of the nucleotide strands constituting the double-stranded nucleic acid may contain a hairpin-shaped DNA described in International Patent Application No. PCT/JP2011/059619, at the 5' end and/or 3' end, preferably 3' end. Specifically, this hairpin-shaped DNA has a structure in which three DNA nucleic acid regions, i.e., a first nucleic acid region, a second nucleic acid region, and a third nucleic acid region, are linked in this order from the 5' end toward the 3' end.

The "first nucleic acid region" refers to a nucleic acid region consisting of arbitrary 2- to 5-mer nucleotides. The bases in this nucleic acid region can be any of guanine, adenine, cytosine, and thymine and are preferably guanine and/or cytosine. This is because a larger gc content can increase a Tm value in the formation of a stem structure with the third nucleic acid region described later, thereby stably maintaining the stem structure. Thus, the whole nucleotide sequence of the first nucleic acid region is most preferably constituted by g and/or c.

The "second nucleic acid region" refers to a nucleic acid region consisting of a nucleotide sequence 5'-gna-3' or 5'-gnna-3'. In the sequence, each n independently represents a natural base (g, a, t, or c), a base analog, or a modified base.

The "third nucleic acid region" refers to a nucleic acid region having a nucleotide sequence complementary to the first nucleic acid region. Thus, the nucleotide sequence of the third nucleic acid region is determined depending on the nucleotide sequence of the first nucleic acid region. The first nucleic acid region and the third nucleic acid region form base pairs in the double-stranded nucleic acid molecule. As a result, the first nucleic acid region and the third nucleic acid region are completely base-paired with each other to constitute a stem structure. Also, the second nucleic acid region positioned between the first nucleic acid region and the third nucleic acid region constitutes a loop structure. A hairpin-shaped DNA of 7 to 14-mer nucleotides having, for example, the nucleotide sequence of SEQ ID NO: 37 or 38 is formed as a whole.

Such a hairpin-shaped DNA can be linked to the 3' end of either or both of the strands in the double-stranded nucleic acid through a phosphodiester bond to thereby improve the resistance of the double-stranded nucleic acid to degradation by a nucleolytic enzyme and enhance its in vivo stability.

<Single-Stranded Nucleic Acid>

The single-stranded nucleic acid constituting the nucleic acid molecule of the present invention forms a secondary structure through intramolecular annealing and intramolecularly has one or more stem structures and one or more loop structures. The double-stranded region is contained in this stem structure. The stem structure may further contain one or more mismatch sites and/or one or more bulge structures.

The nucleotide strand of the single-stranded nucleic acid is not particularly limited by its length as long as the length allows the molecule to contain at least one double-stranded region. The length preferably ranges from, for example, 15 to 100 mer, 20 to 90 mer, or 30 to 80 mer.

Also, the single-stranded nucleic acid can contain the hairpin-shaped DNA described above at its 5' end and/or 3' end, preferably 3' end.

Examples of a preferred form of the nucleic acid molecule of the present invention consisting of the single-stranded nucleic acid include nucleic acid aptamers. A DNA aptamer is particularly preferred in terms of the stability of the nucleic acid.

<DNA Encoding Double-Stranded RNA or Single-Stranded RNA>

The nucleic acid molecule of the present invention may consist of a double-stranded RNA or a single-stranded RNA (e.g., an RNA aptamer). In such a case, a DNA encoding the RNA can also be used. Such a DNA has, for example, a nucleotide sequence derived from the nucleotide sequence constituting the double-stranded RNA or the single-stranded RNA by the substitution of uracil (U) by thymine (T).

The DNA encoding the double-stranded RNA or the single-stranded RNA, for example, a DNA encoding an RNA aptamer, can be prepared through reverse transcription reaction using the RNA aptamer as a template and primers wholly or partially complementary to the 3'-terminal nucleotide sequence of the aptamer. The reverse transcription reaction can be performed using a technique known in the art. The reverse transcription reaction can be performed according to a method described in, for example, Molecular Cloning (supra). Alternatively, the DNA of the present invention may be produced by a chemical synthesis method known in the art on the basis of nucleotide sequence information about the double-stranded RNA and the single-stranded RNA.

The DNA encoding the double-stranded RNA or the single-stranded RNA may be expressibly inserted into an expression vector. The term "expressibly" means that the DNA encoding the double-stranded RNA or the single-stranded RNA is ligated downstream of a promoter in the expression vector so that the RNA concerned can be expressed. A plasmid or a virus capable of autonomously replicating in a host can be used as the expression vector of the present invention. Examples of such a plasmid include: pET, pGEX6p, pMAL, and pREST for host *Escherichia coli* (*E. coli*); pUB110 and pTPS for host *Bacillus subtilis*; YEp13, YEp24, and YCp50 for host yeasts; and binary vectors of pBI series, pRI series, or pGW series for host plants. Examples of the virus include: λ phages (λgt11, λZAP, etc.) for host *E. coli*; retrovirus, adenovirus, adeno-associated virus, and vaccinia virus for host mammals; baculovirus for host insects; and cauliflower mosaic virus (CaMV), bean golden mosaic virus (BGMV), and tobacco mosaic virus (TMV) for host plants.

3-2. Specific Examples of Nucleic Acid Molecule Whose Target Substance is NF-κB

Hereinafter, the nucleic acid molecule of the present invention whose target substance is NF-κB will be described with reference to specific examples.

NF-κB is a transcriptional factor that plays a major role in immune response. This transcriptional factor is involved in inflammatory response, cell growth, and apoptosis, etc. and as such, has received attention as a drug development target. Nucleic acid molecules capable of inhibiting its functions are under development around the world. Examples of such nucleic acid molecules include a decoy DNA comprising a double-stranded DNA fragment having a NF-κB-binding consensus sequence (WO1996/035430; Miyake T., et al., Mol. Ther., 2001, 19: 181-187; Kim K. H., et al., Exp. Mol. Pathol., 2008, 86: 114-120; Isomura I., A. Morita, Microbiol. Immunol., 2006, 50: 559-563; and Mann M. J., Invest., 2000, 106: 1071-1075) and an RNA aptamer (Lebruska L. L. and Maher III L. J., Biochemistry, 1999, 38: 3168-3174; N. J. Reiter, L. J. Maher III, S. E. Butcher, Nucleic Acids Res., 2008, 36: 1227-1236; Chan R., et al., Nucleic Acids Res., 2006, 34, e36; and S. E. Wurster, L. J. Maher III, RNA, 2008, 14: 1037-1047).

Both of these nucleic acid molecules, however, have binding ability (dissociation constant: Kd) of approximately a few nM against NF-κB. By contrast, the nucleic acid molecule of the present invention has binding ability of the order of pM against NF-κB and thus has binding ability at least 100 times higher than that of the known nucleic acid molecules.

The nucleic acid molecule of the present invention whose target substance is NF-κB p50 comprises a double-stranded region consisting of the nucleotide sequences represented by SEQ ID NOs: 1 and 2 shown in FIG. 3A as a consensus sequence. In the nucleotide sequences, the base pair indicated by "W-W" represents "a-t" or "t-a". The symbol "|" between the paired bases in the double-stranded region represents a Watson-Crick base pair. The "open circle" and the "filled circle" between the paired bases represent non-Watson-Crick base pairs consisting of "a-g" or "g-a" and "g-t" or "t-g", respectively. As shown in this diagram, the nucleic acid molecule of the present invention whose target substance is NF-κB p50 has 4 base pairs consisting of non-Watson-Crick base pairs in the consensus sequence consisting of a pair of consecutive 11 bases base-pared with each other. Specific examples of nucleotide sequences contained in such a consensus sequence include the nucleotide sequences represented by SEQ ID NOs: 3 and 4 shown in FIG. 3B, the nucleotide sequences represented by SEQ ID NOs: 5 and 6 shown in FIG. 3C, and the nucleotide sequences represented by SEQ ID NOs: 7 and 8 shown in FIG. 3D.

As mentioned above, the nucleic acid molecule of the present invention whose target substance is NF-κB p50 may be in any form of the double-stranded nucleic acid and single-stranded nucleic acid as long as the molecule comprises one or more double-stranded regions including the consensus sequence described above. For example, the double-stranded nucleic acid may comprise the hairpin-shaped DNA at the 5' end and/or 3' end, preferably 3' end, of the consensus sequence. Preferred examples of the single-stranded nucleic acid include DNA aptamers. Examples thereof include: a DNA aptamer that intramolecularly has the double-stranded region consisting of the nucleotide sequences represented by SEQ ID NOs: 3 and 4 shown in FIG. 3B and comprises a central region represented by any of SEQ ID NOs: 9 to 11 shown in FIG. 4, specifically, for example, clones 5R01, 5R09, and 5R43; a DNA aptamer that intramolecularly has the double-stranded region consisting of the nucleotide sequences represented by SEQ ID NOs: 5 and 6 shown in FIG. 3C and comprises a central region represented by any of SEQ ID NOs: 12 to 18 shown in FIG. 4, specifically, for example, clones 5R14, 5R13, 5R34, 5R10, 5R26, 5R27, and 5R11; and a DNA aptamer that intramolecularly has the double-stranded region consisting of the nucleotide sequences represented by SEQ ID NOs: 7 and 8 shown in FIG. 3D and comprises a central region represented by any of SEQ ID NOs: 19 to 21 shown in FIG. 4, specifically, for example, clones 5R05, 5R28, and 5R19.

3-3. Effect

These DNA aptamers have, as shown below in Examples, binding ability at least 100 to 1000 times stronger than that of conventionally known RNA aptamers or DNA aptamers whose target substance is NF-κB p50. Thus, the nucleic acid molecule of the present invention can drastically improve the binding ability of the conventional nucleic acid aptamers against the target substance, because at least one double-stranded region contained in the nucleic acid molecule has non-Watson-Crick base pairs.

4. Inhibitor of Target Substance Function

The third embodiment of the present invention relates to an inhibitor of target substance function.

4-1. Constitution

The inhibitor of target substance function of the present invention comprises the nucleic acid molecule according to the second embodiment as an active ingredient.

In the present specification, the "inhibition of target substance function" refers to the inhibition or suppression of biological functions of the target substance, such as catalytic functions, gene expression control functions (including the control of transcription, translation, transport, etc.), or apoptosis control functions, through the binding of the nucleic acid molecule serving as an active ingredient.

The content of the nucleic acid molecule in the inhibitor of target substance function of the present invention can be a pharmaceutically effective amount.

In the present specification, the "pharmaceutically effective amount" refers to a dose required for the nucleic acid molecule of the second embodiment serving as an active ingredient in the inhibitor of target substance function to exert its efficacy (inhibition of target substance function) and refers to a dose that exhibits no or few adverse reactions or side effects on a recipient organism or the like. The specific amount differs depending on the type of the target substance, the suppressive activity of the nucleic acid molecule, the dosage form used, and (for the purpose of administration to an organism) information about the organism (test subject) and an administration route. Specific examples of the administration to an organism include administration to humans. In this case, the range of the pharmaceutically effective amount and a suitable administration route are generally set on the basis of data obtained from cell culture assay and animal experiments. The dose is finally determined and adjusted at a physician's discretion according to individual test subjects. In this respect, information to be considered about the test subjects includes, for example, the degree of progression or severity of disease, general health conditions, age, body weight, sex, diet, drug sensitivity, and resistance to treatment.

The content of the nucleic acid molecule of the present invention per dosage unit of the inhibitor of target substance function can be, for example, approximately 0.01% (w/v) to approximately 20% (w/v), preferably approximately 0.1% (w/v) to approximately 10% (w/v), in terms of the content of the nucleic acid molecule of the present invention whose target substance is NF-κB p50 per dosage unit of an injection solution to be administered to an adult human male (body weight: 60 kg) that does not require combined use with another pharmaceutical drug. When the nucleic acid of the present invention needs to be administered in large amounts for obtaining the pharmacological effect of the inhibitor of the present invention, the inhibitor may be administered at several divided doses in order to reduce burdens on the test subject.

5. Pharmaceutical Composition

The fourth embodiment of the present invention relates to a pharmaceutical composition.

5-1. Constitution

The pharmaceutical composition of the present invention comprises at least one inhibitor of target substance function according to the third embodiment. Also, the pharmaceutical composition of the present invention may contain a pharmaceutically acceptable support. The "pharmaceutically acceptable support" refers to a substance that is usually used in the pharmaceutical formulating art and added without inhibiting or suppressing the effect of the pharmaceutical composition in order to facilitate the formulation of the pharmaceutical composition or its application to organisms and maintain the effect of the inhibitor of target substance function. Examples of the support include excipients, binders, disintegrants, fillers, emulsifiers, flow control additives, lubricants, and surfactants.

Examples of the "excipients" include sugars such as monosaccharides, disaccharides, cyclodextrin, and polysaccharides (specifically including, but not limited to, glucose, sucrose, lactose, raffinose, mannitol, sorbitol, inositol, dextrin, maltodextrin, starch, and cellulose), metal salts (e.g., sodium phosphate or calcium phosphate, calcium sulfate, and magnesium sulfate), citric acid, tartaric acid, glycine, low-, middle-, or high-molecular-weight polyethylene glycol (PEG), Pluronic, and combinations thereof.

Examples of the "binders" include starch glues composed of corn, wheat, rice, or potato starch, gelatin, tragacanth, methylcellulose, hydroxypropylmethylcellulose, sodium carboxymethylcellulose, polyvinylpyrrolidone, and combinations thereof.

Examples of the "disintegrants" include the starches described above, carboxymethyl starch, cross-linked polyvinylpyrrolidone, agar, alginic acid or sodium alginate, and salts thereof.

Examples of the "fillers" include the sugars described above, calcium phosphate (e.g., tricalcium phosphate or calcium hydrogen phosphate), and combinations thereof.

Examples of the "emulsifiers" include sorbitan fatty acid ester, glycerin fatty acid ester, sucrose fatty acid ester, and propylene glycol fatty acid ester.

Examples of the "flow control additives" and the "lubricants" include silicate, talc, stearate, and polyethylene glycol.

Such supports can be used appropriately according to the need. The pharmaceutical composition of the present invention may also contain, in addition to the additives described above, optional additives such as corrigents, solubilization aids (solubilizers), suspending agents, diluents, surfactants, stabilizers, absorption promoters (e.g., quaternary ammonium salts and sodium lauryl sulfate), expanders, wetting agents, humectants (e.g., glycerin and starch), adsorbents (e.g., starch, lactose, kaolin, bentonite, and colloidal silicic acid), disintegration inhibitors (e.g., saccharose, stearin, cacao butter, and hydrogenated oil), coating agents, coloring agents, preservatives, antioxidants, fragrances, flavors, sweeteners, and buffers.

The "surfactants" correspond to, for example, alkali metal salts, alkaline earth metal salts, and ammonium salts of lignosulfonic acid, naphthalenesulfonic acid, phenolsulfonic acid, or dibutylnaphthalenesulfonic acid, alkylaryl sulfonate, alkyl sulfate, alkyl sulfonate, fatty alcohol sulfate, fatty acid and sulfated fatty alcohol glycol ether, condensates of sulfonated naphthalene or naphthalene derivatives and formaldehyde, condensates of naphthalene or naphthalenesulfonic acid, phenol, and formaldehyde, polyoxyethylene octylphenyl ether, ethoxylated isooctylphenol, octylphenol, nonylphenol, alkylphenyl polyglycol ether, tributylphenyl polyglycol ether, tristearylphenyl polyglycol ether, alkylaryl polyether alcohol, alcohol and fatty alcohol/ethylene oxide condensates, ethoxylated castor oil, polyoxyethylene alkyl ether, ethoxylated polyoxypropylene, lauryl alcohol polyglycol ether acetal, sorbitol ester, lignosulfite waste liquors, and methylcellulose.

The pharmaceutical composition of this embodiment may contain at least one of these supports.

The pharmaceutical composition of the present invention can further contain an additional drug without canceling the pharmacological effect of the nucleic acid of the present invention. The pharmaceutical composition of the present invention may contain, for example, a predetermined amount of an antibiotic.

The pharmaceutical composition of the present invention is not particularly limited by its dosage form as long as the form does not deactivate the active ingredient and can exert the pharmacological effect in vivo after administration. The dosage form usually differs depending on an administration method and/or prescription conditions.

Examples of dosage forms suitable for oral administration can include solid preparations (including tablets, pills, sublingual preparations, capsules, drops, and troches), granules, dusts, powders, and liquid preparations. The solid preparations can be prepared, if necessary, in coated dosage forms known in the art, for example, as sugar-coated tablets, gelatin-coated tablets, enteric coated tablets, film-coated tablets, bilayer tablets, or multilayer tablets.

Parenteral administration is subdivided into systemic administration and local administration. The local administration is further subdivided into interstitial administration, transepidermal administration, transmucosal administration, and transrectal administration. The pharmaceutical composition can also be prepared in a dosage form suitable for each administration method. Examples of dosage forms suitable for systemic or interstitial administration include injections which are liquid preparations. Examples of dosage forms suitable for transepidermal administration or transmucosal administration can include liquid preparations (including liniments, eye drops, nasal drops, and inhalants), suspensions (including emulsions and creams), dusts (including nasal drops and inhalants), pastes, gels, ointments, and plasters. Examples of dosage forms suitable for transrectal administration can include suppositories.

In the case of drug administration to plants, examples of the dosage form of the pharmaceutical composition include liquids, solids (including semi-solids), and combinations thereof. In this case, the pharmaceutical composition can be prepared as solutions, oil dispersions, emulsions, suspensions, dusts, powders, pastes, gels, pellets, tablets, and granules.

These dosage forms are not particularly limited by their specific shapes or sizes and can have any shape or size that falls within ranges accepted for each dosage form known in the art.

5-2. Production Method

The pharmaceutical composition of the present invention can be produced by the application of a formulation method known in the art, as a rule. See a method described in, for example, Remington's Pharmaceutical Sciences (Merck Publishing Co., Easton, Pa.).

For example, the injection can be produced by a method routinely used in the art which involves dissolving the nucleic acid molecule of the second embodiment in a pharmaceutically acceptable solvent and adding, if necessary, a pharmaceutically acceptable support to the resulting solution.

Examples of the "pharmaceutically acceptable solvent" include water, ethanol, propylene glycol, ethoxylated isostearyl alcohol, polyoxygenated isostearyl alcohol, and polyoxyethylene sorbitan fatty acid esters. Desirably, such a solvent is sterilized and preferably adjusted, if necessary, to be isotonic to blood.

5-3. Administration Method

The pharmaceutical composition of this embodiment can be administered to an organism in a pharmaceutically effective amount for the treatment or prevention of the disease of interest or the like. The recipient organism is a vertebrate, preferably a mammal, more preferably a human.

The pharmaceutical composition of the present invention may be administered systemically or locally. An appropriate route can be selected according to, for example, the type, site of onset, or degree of progression of the disease. For a disease whose onset is localized to a site, local administration is preferred in which the pharmaceutical composition of the present invention is directly administered to the site of onset and its neighborhood through injection or the like. This is because the nucleic acid molecule of the present invention can be delivered in sufficient amounts to the site (tissue or organ) to be treated with little influence on the other tissues. For a disease whose site to be treated cannot be identified or a disease whose onset is systemic, systemic administration through intravenous injection or the like is preferred, though the administration route is not limited thereto. This is because the nucleic acid molecule of the present invention can be distributed throughout the body via blood flow and thereby delivered even to a lesion that cannot be found by diagnosis.

The pharmaceutical composition of the present invention can be administered by any appropriate method without deactivating the active ingredient. For example, any of parenteral (e.g., injection, aerosol, application, eye drop, and nasal drop) and oral administrations can be performed. Injection is preferred.

In the case of administration through injection, an injection site is not particularly limited. The injection site may be any site at which the nucleic acid molecule serving as an active ingredient can bind to the target substance to thereby suppress its functions. Examples thereof include intravenous, intraarterial, intrahepatic, intramuscular, intraarticular, intramedullary, intraspinal, intraventricular, transpulmonary, transdermal, hypodermic, intradermal, intraperitoneal, intranasal, enteral, and sublingual injections. Intravascular injection such as intravenous injection or intraarterial injection is preferred. This is because, as described above, the pharmaceutical composition of the present invention can be distributed throughout the body via blood flow and also because this injection is relatively low invasive.

6. Method for Detecting Target Substance

The fifth embodiment of the present invention relates to a method for detecting a target substance using the nucleic acid molecule according to the second embodiment.
6-1. Constitution The nucleic acid molecule according to the second embodiment is capable of very strongly and specifically binding to its target substance. The target substance present in a sample can therefore be detected by use of this property of the nucleic acid molecule.

The detection method itself can be any detection method known in the art as long as the method is based on the binding between the nucleic acid molecule according to the second embodiment and the target substance. For example, a SPR method, a quartz crystal microbalance method, turbidimetry, colorimetry, or fluorometry can be used.

SPR (surface plasmon resonance) refers to a phenomenon in which as a thin metal film is irradiated with laser beam, reflected light intensity remarkably attenuates at a particular angle of incidence (resonance angle). The SPR method is an assay method based on this phenomenon and is capable of highly sensitively assaying a substance adsorbed on the surface of the thin metal film serving as a sensor portion. In the present invention, for example, the nucleic acid molecule of the second embodiment is immobilized in advance onto the surface of a thin metal film. A sample is flowed on the thin metal film surface to allow the target substance to bind to the nucleic acid molecule. The resulting difference in the substance adsorbed on the metal surface between before and after the sample flowing can be detected to thereby detect the target substance in the sample. SPR methods such as a displacement method and an indirect competitive method are known, any of which may be used in the present invention.

The quartz crystal microbalance (QCM) method refers to a method using a phenomenon in which the resonance frequency of a quartz crystal decreases according to the mass of the substance adsorbed onto the surface of electrodes attached to the quartz crystal. A QCM sensor based on this method can quantitatively capture a trace amount of the adsorbed substance according to the amount of change in the resonance frequency of a quartz crystal. In the present invention, the nucleic acid molecule is immobilized in advance, as in the SPR method, onto the electrode surface. A sample is contacted with the electrode surface. The target substance in the sample can be quantitatively detected from the amount of change in the resonance frequency of a quartz crystal caused by the binding between the nucleic acid molecule and the target substance. This technique is well known in the art. See, for example, Christopher J., et al. (2005), Self-Assembled Monolayers of a Form of Nanotechnology, Chemical Review, 105: 1103-1169.

The turbidimetry refers to a method which involves irradiating a solution with light and optically measuring the attenuation of light scattered by a substance floating in the solution or light transmitted through the solution using a colorimeter or the like to determine the amount of the substance in the solution. In the present invention, absorbance can be measured before and after addition of the nucleic acid molecule of the second embodiment into a sample to thereby quantitatively detect the target substance in the sample.

Alternatively, the target substance may be detected by combined use with an antibody against the target substance. For example, a method based on sandwich ELISA may be used. This method involves first immobilizing the nucleic acid molecule of the second embodiment onto a solid-phase support and next adding a sample thereto to allow the nucleic acid molecule to bind to the target substance present in the sample. Subsequently, the sample is washed off. Then, the anti-target substance antibody is added thereto and allowed to bind to the target substance. After washing, the anti-target substance antibody can be detected using an appropriately labeled secondary antibody to thereby detect the target substance in the sample. An insoluble support in the form of, for example, beads, a microplate, a test tube, a stick, or a test piece made of a material such as polystyrene, polycarbonate, polyvinyltoluene, polypropylene, polyethylene, polyvinyl chloride, nylon, polymethacrylate, latex, gelatin, agarose, cellulose, Sepharose, glass, a metal, a ceramic, or a magnetic material can be used as the solid-phase support.

Specific examples of such a detection method include a method for detecting NF-κB p50 as the target substance using the nucleic acid molecule according to the second embodiment that comprises a double-stranded region consisting of the nucleotide sequences represented by SEQ ID NOs: 1 and 2 shown in FIG. 3A as a consensus sequence. Alternative examples thereof include a detection method using a nucleic acid molecule having the nucleotide sequences represented by SEQ ID NOs: 3 and 4 shown in FIG. 3B, the nucleotide sequences represented by SEQ ID NOs: 5 and 6 shown in FIG. 3C, or the nucleotide sequences represented by SEQ ID NOs: 7 and 8 shown in FIG. 3D, specifically, for example, a nucleic acid molecule comprising the hairpin-shaped DNA described in the second embodiment at the 5' end and/or 3' end, preferably 3' end, of the consensus sequence or a DNA aptamer comprising a central region represented by any of SEQ ID NOs: 9 to 21 shown in FIG. 4, more specifically, for example, clones 5R01, 5R09, 5R43, 5R14, 5R13, 5R34, 5R10, 5R26, 5R27, 5R11, 5R05, 5R28, and 5R19. If the nucleic acid molecule cannot be used due to high nuclease concentration in a sample, the sample can be treated with a nuclease inhibitor or the like before assay and then used.
6-2. Effect The detection method of the present invention is capable of highly sensitively detecting a small amount of a target substance in a sample by use of the strong and specific binding of the nucleic acid molecule of the second embodiment to the target substance.

7. NF-κB p50 Detection Kit

The sixth embodiment of the present invention relates to a kit for NF-κB p50 detection comprising at least one NF-κB p50-binding nucleic acid molecule of the second embodiment. This kit can detect NF-κB p50 in a sample by use of the NF-κB p50-binding nucleic acid described in the above aspect.

This kit can optionally contain, for example, a labeled secondary antibody, a substrate necessary for the detection of the label, a positive control, a negative control, or a buffer solution for use in sample dilution or washing, in addition to the NF-κB p50-binding aptamer according to the second embodiment. The kit may further contain an instruction manual.

EXAMPLES

Example 1: Development of Method for Highly Efficiently Producing Nucleic Acid Aptamer I. Study on Conditions for Solid-Phase Support The method for producing a nucleic acid aptamer according to the present invention was studied for the optimum conditions for a solid-phase support for reducing the nonspecific adsorption of single-stranded nucleic acids onto the solid-phase support used.

(Method)

The solid-phase supports used were two types of streptavidin-coated magnetic beads commercially available from a manufacturer. Magnetic beads A (New England Biolabs Inc., Hydrophilic Streptavidin Magnetic Beads) have hydrophilic surface, while magnetic beads B (New England Biolabs Inc., Streptavidin Magnetic Beads) have hydrophobic surface.

These magnetic beads were used to test the nonspecific adsorption of single-stranded DNAs onto the magnetic beads. Specifically, a solution containing 8 pmoL of a single-stranded nucleic acid library (total length of single-stranded nucleic acid: 79 mer) constituted by single-stranded DNAs (SEQ ID NO: 22) each comprising a 43-base random region (indicated by N) was mixed with 50 μg of the magnetic beads A or B. Then, the magnetic beads were washed with 40 mL of a PBS buffer containing 0.05% Nonidet P-40 and 2.5 mM DTT using a 50-mL Falcon tube to remove the single-stranded DNAs in the solution. Then, the amount of DNAs nonspecifically adsorbed on the magnetic beads was detected by real-time PCR. The real-time PCR was performed using a reverse primer represented by SEQ ID NO: 23 and a forward primer represented by SEQ ID NO: 24. The reverse primer, which was complementary to each single-stranded DNA constituting the library, was modified at 5'-terminal thymine (t) with biotin. Hence, PCR-amplified products were mixed with streptavidin and then subjected to denaturing gel electrophoresis. Amplification products of the single-stranded DNAs of interest can be selectively prepared by the gel shift method, because unreacted reverse primers and complementary sequences of the 5'-terminally biotinylated single-stranded DNAs (SEQ ID NO: 22) bind to streptavidin and exhibit slow mobility.

The reaction conditions of PCR involved 30 PCR cycles each involving 3 steps (95° C. for 30 seconds, 50° C. for 30 seconds, and 65° C. for 2 minutes) in the presence of SYBR Green I (Lonza Group Ltd.) and ROX Dye (Life Technologies Corp.). The amplification course was detected using Mx3005P (Agilent Technologies, Inc.).

(Results)

Figure 5:
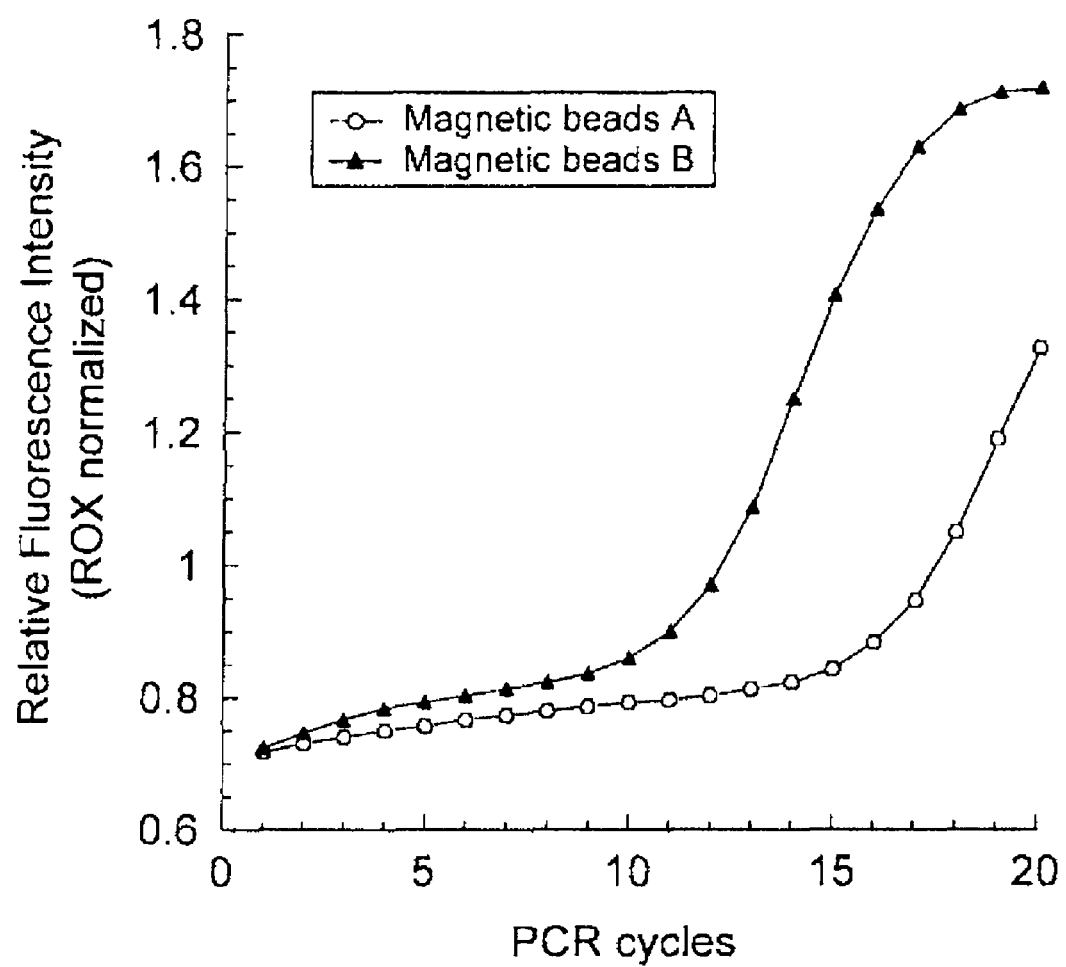
FIG. 5 shows results of detecting the nonspecific adsorption of single-stranded DNAs onto various magnetic beads as solid-phase supports by real-time PCR.
Figure 6:
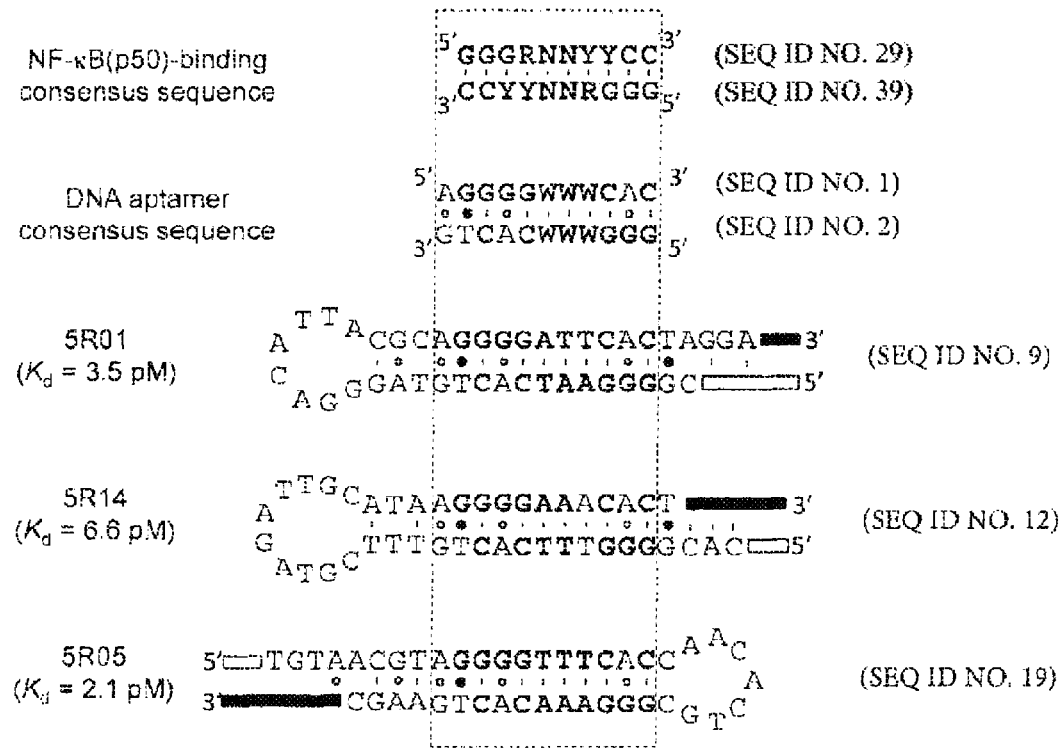
FIG. 6 shows the consensus sequences and secondary structures of three clones (5R01, 5R14, and 5R05) among the NF-κB p50-binding DNA aptamers shown in FIG. 4, and the dissociation constant (Kd) of each clone for NF-κB p50. The uppermost sequence represents a NF-κB p50-binding consensus sequence known in the art. The open box represents a 5'-terminal primer-binding region. The filled box represents a 3'-terminal primer-binding region.

The results are shown in FIG. 5. As shown in this diagram, the magnetic beads B having hydrophobic surface yielded a larger number of amplification products than that by the magnetic beads A having hydrophilic surface. These results demonstrated that a solid-phase support having hydrophilic surface causes the smaller nonspecific adsorption of single-stranded nucleic acids and is more suitable as the solid-phase support of the production method of the present invention, compared with a solid-phase support having hydrophobic surface.

The addition of the nonpolar surfactant such as Nonidet P-40 into the buffer used in the washing of the magnetic beads was shown to improve the collectability of the magnetic beads as the solid-phase support, compared with the absence of the nonpolar surfactant (data not shown).

II. Production of DNA Aptamer Whose Target Substance is NF-κB p50

Next, DNA aptamers strongly binding to a transcriptional factor NF-κB p50 as a target substance were prepared using the method for producing a nucleic acid aptamer according to the present invention.

(Method)

The repetitive step (106) described later of the round from the complex formation step (101) to the single-stranded nucleic acid preparation step (105) was performed using a single-stranded nucleic acid library (total length of single-stranded nucleic acid: 95 mer) constituted by chemically synthesized single-stranded DNAs (SEQ ID NO: 25) comprising a central region (indicated by N) each having a 43-base random nucleotide sequence.

Hereinafter, each step in the production method of the present invention will be described specifically.

(1) Complex Formation Step (101)

The single-stranded nucleic acid library was dissolved in a PBS buffer solution (1.1 mM $KH_2PO_4$, 155 mM NaCl, and 3 mM $Na_2HPO_4$, pH 7.4). In order to form the intramolecular conformations of single-stranded DNAs, the solution was subjected to heating-cooling treatment which involved heating at 90° C. for 3 minutes, then cooling at 60° C. for 3 minutes, and then leaving at 25° C. Then, this solution was mixed with an equal amount of a PBS buffer solution containing 0.1% Nonidet P-40 and 5 mM DTT.

Next, magnetic beads were pretreated as a solid-phase support. The magnetic beads used were magnetic beads A (Hydrophilic Streptavidin Beads, New England Biolabs Inc.) in light of the results of the paragraph "I. Study on conditions for solid-phase support". In order to exclude single-stranded DNAs that were nonspecifically adsorbed onto the magnetic beads from the single-stranded nucleic acid library, the single-stranded nucleic acid library solution was incubated at room temperature for 30 minutes with 0.2 mg of streptavidin-coupled magnetic beads (Hydrophilic Streptavidin Beads, New England Biolabs Inc.). The magnetic beads were removed using a magnet stand and centrifugation operation, and the supernatant fluid was recovered.

Then, the supernatant fluid was mixed with recombinant human NF-κB p50 (rhNF-κB, Promega Corp.) as a target protein at a ratio described in Table 1. The mixture was incubated at 25° C. for 30 minutes to form a complex of a single-stranded DNA and NF-κB p50. The ratio between the concentrations of the single-stranded nucleic acid library and NF-κB p50 for complex formation, the volume of the reaction solution used in this step, and the like, were adjusted on a round basis. The details will be described later in the repetitive step (106).

TABLE 1

Production conditions for NF-κB-binding DNA aptamer in each round

| Round | ssDNA pool pmol | ssDNA pool nM | NF-κB p50 (in terms of monomer) pmol | NF-κB p50 (in terms of monomer) nM | Competitive DNA molecule NF-κB Mini46 pmol | Competitive DNA molecule NF-κB Mini46 nM | Washing with buffer containing 3M urea | Binding scale (μL) |
|---|---|---|---|---|---|---|---|---|
| 1 | 333 | 728 | 35 | 78 | 0 | 0 | Absent | 450 |
| 2 | 6 | 40 | 6 | 40 | 0 | 0 | Absent | 150 |
| 3 | 2 | 20 | 2 | 20 | 20 | 200 | Absent | 100 |
| 4 | 2 | 2 | 2 | 2 | 200 | 200 | Absent | 1000 |
| 5 | 2 | 2 | 2 | 2 | 200 | 200 | Present | 1000 |

Binding conditions: PBS, 2.5 mM DTT, 0.05% Nonidet P-40 (25° C., 30 min.)

(2) Immobilization Step (102)

In this Example, biotin and streptavidin were used as connectors. Biotin corresponds to the first connector adsorbed on a target substance. Streptavidin corresponds to the second connector adsorbed on the magnetic beads.

Since the NF-κB p50 used was not biotinylated, 0.09 volumes of a 10 mM biotinylating reagent (EZ-link Sulfo-NHS-LC-Biotin, Thermo Fischer Scientific Inc.) was first added to the solution after the complex formation, and the mixture was incubated at 25° C. for 15 minutes. This procedure biotinylated NF-κB p50 contained in the complex in the solution and uncomplexed free NF-κB p50.

In order to prevent increase in background, unreacted biotinylating reagents were removed by washing operation using ultrafiltration through Microcon 50 (Merck KGaA).

The biotinylated complex-containing solution thus washed was mixed with streptavidin-coupled magnetic beads (Hydrophilic Streptavidin Beads, New England Biolabs Inc.) (6.8 to 8 μg/pmol in terms of p50 monomer), and the mixture was incubated at room temperature for 10 minutes to immobilize the complexes onto the magnetic beads via the biotin and streptavidin connectors. In order to wash off single-stranded DNAs nonspecifically adsorbed on the proteins or the magnetic beads, the magnetic beads were then suspended in 40 mL of a PBS buffer containing 0.05% Nonidet P-40 and 2.5 mM DTT (hereinafter, referred to as "buffer A" in the present specification) and incubated for 30 minutes with stirring at 37° C. This washing operation was repeated again.

(3) Recovery Step (103)

400 μL of an eluent (100 mM sodium citrate, pH 5.0, 7 M urea, and 3 mM EDTA) was added to the magnetic beads after the immobilization step (102), and the mixture was heated at 90° C. for 5 minutes, followed by recovery of an eluate. Then, this recovered eluate was treated with phenol-chloroform. The single-stranded DNAs were recovered from the complexes with NF-κB p50 by isopropyl alcohol precipitation operation.

(4) Amplification Step (104)

A reverse primer represented by SEQ ID NO: 26 and a forward primer represented by SEQ ID NO: 27 were used in PCR. The reverse primer was modified at 5'-terminal thymine (t) with biotin. PCR was performed using Ex Taq DNA polymerase (Takara Bio Inc.) having a final concentration of 0.025 U/μL and a buffer attached thereto. The reaction composition was prepared as 2 mM $MgCl_2$ and 0.2 mM dNTPs (N=A, G, C, or T) (these concentrations were final concentrations). The cycle conditions were 15 cycles or 20 cycles (according to the amount of DNAs amplified) each involving 3 steps (94° C. for 30 seconds, 50° C. for 30 seconds, and 72° C. for 1 minute).

(5) Single-Stranded Nucleic Acid Preparation Step (105)

Double-stranded DNAs were recovered by ethanol precipitation from the PCR solution containing the amplification products after the amplification step (104) and then prepared into single-stranded DNAs by the gel shift method using streptavidin. Specifically, the recovered double-stranded DNAs (0.4 mL of the PCR solution) were suspended in 10 μL of an SA buffer solution (10 mM Tris-HCl pH 7.6, 50 mM NaCl, and 1 mM EDTA) and heated at 75° C. for 3 minutes. Then, 10 μL of a streptavidin solution (5 mg/mL, dissolved in an SA buffer solution) was added thereto, and the mixture was incubated at 25° C. for 30 minutes. Since the reverse primer used in the amplification step (104) was biotinylated at the 5'-terminal base, this operation forms a complex of a biotinylated double-stranded DNA and avidin. To this complex-containing solution, the same volume of a loading buffer for denaturing gel (10 M urea and 1× TBE solution) was added, and the mixture was heated at 75° C. for 3 minutes to make the double-stranded DNAs into single strands, followed by electrophoresis on a 6% polyaramide denaturing gel containing 7 M urea. The amplified single-stranded DNAs of interest were recovered from the gel to remove unnecessary biotinylated single-stranded DNAs. The obtained single-stranded DNAs were dissolved in a PBS buffer solution (1.1 mM $KH_2PO_4$, 155 mM NaCl, and 3 mM $Na_2HPO_4$, pH 7.4). The solution was subjected to heating-cooling treatment which involved heating at 90° C. for 3 minutes, then cooling at 60° C. for 3 minutes, and then leaving at 25° C. to form the intramolecular conformations of the single-stranded DNAs. Then, this solution was mixed with an equal amount of a PBS buffer solution containing 0.1% Nonidet P-40 and 5 mM DTT. The obtained single-stranded DNAs were used as a new single-stranded nucleic acid library in the next round.

(6) Repetitive Step (106)

In this Example, 5 rounds of this step were performed. Conditions such as the concentrations of the single-stranded nucleic acid library and the target substance NF-κB p50 in each round were as shown above in Table 1.

The single-stranded nucleic acid library constituted by the single-stranded DNAs prepared by chemical synthesis and gel purification as mentioned above was directly used in the first round. In this round, the total number of molecular species of the single-stranded DNAs used was 333 pmol. This corresponds to approximately $2 \times 10^{13}$ molecules of single-stranded DNAs. In the course of repeated rounds, the concentrations of the single-stranded nucleic acid library and NF-κB p50 were gradually decreased to render the single-stranded DNA-NF-κB p50 complex formation conditions stricter. In round 3 or later, an excessive amount of NF-κB mini46 (46 mer) was added as a competitive DNA molecule (SEQ ID NO: 28) during complex formation by the mixing of the single-stranded nucleic acid library with NF-κB p50. At the completion of each round, washing at 37° C. for 30 minutes was performed twice using 40 mL of buffer A. Only in round 5, however, washing at room temperature for 15 minutes was performed by inverting and mixing using 1 mL of buffer A further supplemented with 3 M urea. This rendered the washing conditions stricter to screen for single-stranded DNA fragments strongly binding to NF-κB p50.

(7) Identification of NF-κB p50-Binding DNA Aptamer

The central region in each single-stranded DNA obtained after the completion of 5 rounds was sequenced to identify the primary structures of the obtained NF-κB p50-binding DNA aptamers and secondary structures predicted from their nucleotide sequences.

First, 15 cycles of PCR were performed at a reaction scale of 50 μL under the same reaction composition and cycle conditions as in the amplification step (104) using a portion of each single strand recovered after the completion of 5 rounds as a template and unbiotinylated primers represented by SEQ ID NOs: 26 and 27. Then, an aliquot (2 μL) of the amplification products was cloned using a TOPO TA cloning kit (Life Technologies Corp.). Plasmids were recovered from the obtained E. coli clones, and 42 clones were sequenced to determine the nucleotide sequences of the central regions.
(Results)

FIG. 4 shows the nucleotide sequences, clone names, the numbers of clones, and SEQ ID NOs of the obtained NF-κB p50-binding DNA aptamers. As shown in this diagram, the nucleotide sequences of the central regions were largely classified into three sequence groups: a sequence group having the nucleotide sequences represented by SEQ ID NOs: 9 to 11, a sequence group having the nucleotide sequences represented by SEQ ID NOs: 12 to 18, and a sequence group having the nucleotide sequences represented by SEQ ID NOs: 19 to 21. Each sequence contained a sequence analogous to the NF-κB-binding natural consensus DNA sequence represented by SEQ ID NO: 29. These sequences analogous to the consensus sequence were confirmed, as shown in FIG. 5, to be positioned at the stem sites of hairpin structures. Interestingly, the sequence of this stem site, unlike the natural DNA sequence, was shown to contain non-Watson-Crick base pairs of G-A and G-T.

Example 2: Binding Ability of DNA Aptamer Binding to NF-κB

Of the NF-κB p50-binding DNA aptamer clones obtained in Example 1, 5R01, 5R14, and 5R05 (see FIG. 4) obtained with larger numbers of clones in the sequence groups were used to analyze their NF-κB p50-binding ability.
(Method)

The single-stranded DNA (total length: 95 mer) of each clone was prepared by PCR amplification using the plasmid of the clone obtained in Example 1 as a template and biotinylated primers of SEQ ID NOs: 26 and 27, followed by the gel shift method using streptavidin by the same procedures as in the single-stranded nucleic acid preparation step shown in Example 1.

The binding ability of each NF-κB p50-binding DNA aptamer clone for NF-κB p50 was determined by the surface plasmon resonance (SPR) method using BIACORE 3000 (GE Healthcare Japan Corp.). The assay in the SPR method was conducted with a temperature set to 25° C. using buffer A as a running buffer. Specifically, DNA probes (21 mer) (SEQ ID NO: 30) each having a nucleotide sequence complementary to the 3'-terminal region of each clone and having a biotinylated base at the 5' end were immobilized onto a streptavidin-coated sensor chip (SA chip). Then, 60 μL (corresponding to 12 minutes) of a solution of each single-stranded DNA clone (95 mer) diluted to 50 nM with PBS was injected thereto at a flow rate of 5 μL/min to immobilize the clone onto the SA chip through hybridization with the probe.

The association and dissociation between the immobilized clone DNA and NF-κB p50 were detected by monitoring after injection of a 2.5 nM or 5 nM NF-κB p50 solution (diluted with buffer A; in terms of dimer) at the Kinetic Injection mode. The assay conditions involved a flow rate of 20 μL/min, protein injection for 6 minutes, and protein dissociation assay for 6 minutes after the completion of the injection. The chip was regenerated (protein binding was dissociated) by the injection of 5 μL (corresponding to 15 seconds) of a 2 M NaCl solution. The DNAs immobilized by hybridization can be removed by the injection of 5 μL (corresponding to 12 seconds) of a 0.05 M NaOH solution at a flow rate of 25 μL/min. Thus, binding analyses respectively using different DNA sequences were able to be conducted using the same chip.
(Results)

Figure 7:
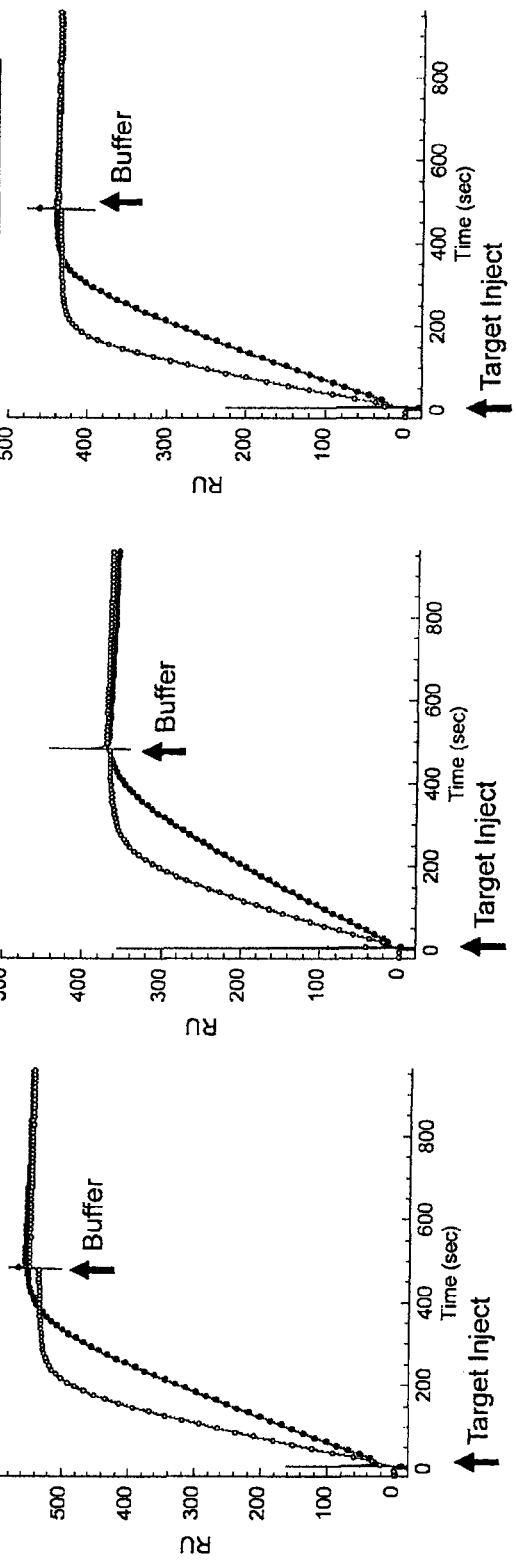
FIGS. 7A-7C shows a surface plasmon resonance (SPR) sensorgram of the detected interaction between each of three NF-κB p50-binding DNA aptamer clones (5R01 (FIG. 7A), 5R14 (FIG. 7B), and 5R05 (FIG. 7C)) produced by the method of the present invention and NF-κB p50.

The results are shown in FIGS. 7A-7C. This diagram is a sensorgram of the detected interaction between each of the above three clones and NF-κB p50. As is evident from this diagram, all the clones very strongly bind to NF-κB p50, and the associated clones are dissociated very late from NF-κB p50 as shown in sensorgram patterns obtained after the completion of the NF-κB p50 injection. The dissociation constant Kd was calculated by fitting in reaction model 1:1 binding with mass transfer using analysis software attached to BIACORE 3000 and consequently was Kd=2.1 to 3.5 pM with a dissociation rate constant of the order of $10^{-5}$ (1/s).

Example 3: Binding Ability of DNA Aptamer Variant Binding to NF-κB p50

Truncated variants of the NF-κB p50-binding DNA aptamer clones 5R01, 5R14, and 5R05 tested in Example 2 were analyzed for their NF-κB p50-binding ability.
(Method)

Figure 8:
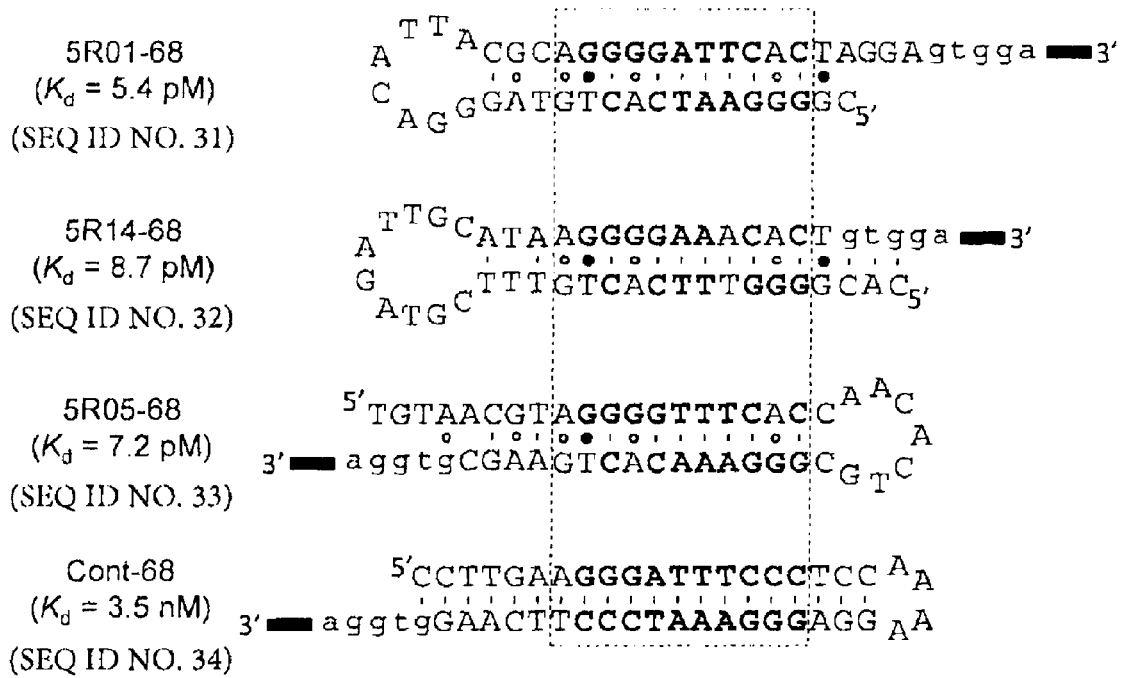
FIG. 8 shows the nucleotide sequences and secondary structures of single-stranded DNA variants (5R01-68, 5R14-68, and 5R05-68; free from a sequence comprising the 5'-terminal primer sequence region) of each NF-κB p50-binding DNA aptamer clone shown in FIGS. 7A-7C, and Cont-68 for control (comprising a NF-κB p50-binding consensus sequence known in the art) free from non-Watson-Crick base pairs.
Figure 9A:
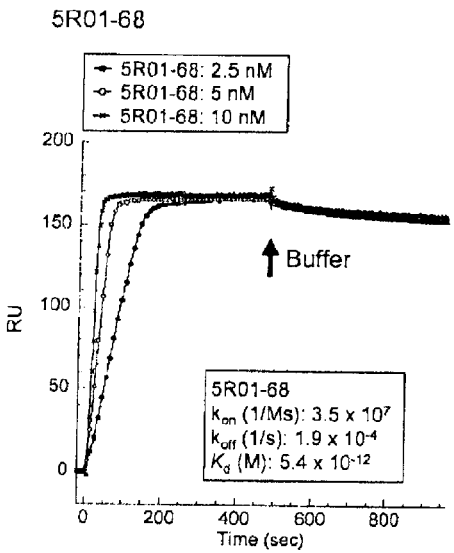
FIGS. 9A-9D show a SPR sensorgram of the detected interaction between each of three clones (5R01 (FIG. 9A), 5R14 (FIG. 9B), and 5R05 (FIG. 9C)) or Cont-68 (FIG. 9D) for control shown in FIG. 8 and NF-κB p50.
Figure 9B:
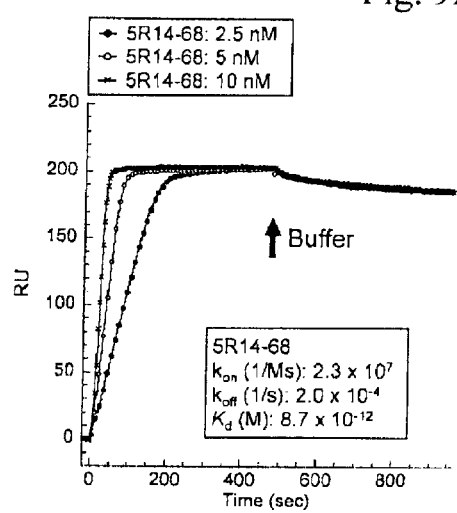
Figure 9C:
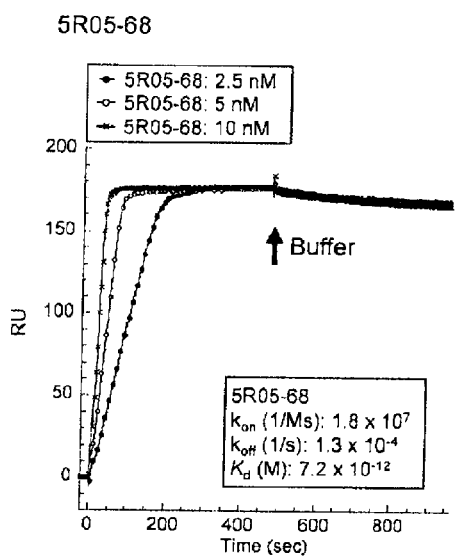
Figure 9D:
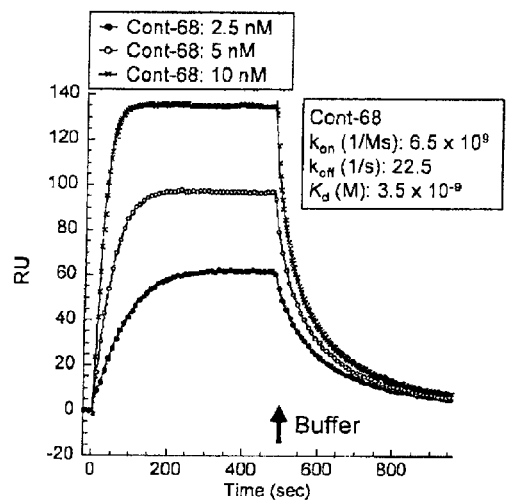

Single-stranded DNA variants (68 mer, SEQ ID NOs: 31, 32, and 33; free from a sequence comprising the 5'-terminal primer sequence region) of each NF-κB p50-binding DNA aptamer clone were analyzed for their binding ability by the same SPR method as in Example 2. FIG. 8 shows the sequence of each DNA fragment. These single-stranded DNA variants used in binding analysis were prepared by chemical synthesis and gel purification. In the diagram, Cont-68 (SEQ ID NO: 34) corresponds to a single-stranded DNA in which the strands of a double-stranded DNA comprising a known NF-κB p50-binding consensus sequence were linked via adenine tetraloop (AAAA). For SPR analysis, each of these single-stranded DNAs was immobilized onto the SA chip through hybridization with probes by the injection of 20 μL (corresponding to 1 minute) of a solution of each DNA fragment (68 mer) diluted to 250 nM with PBS at a flow rate of 20 μL/min.
(Results)

The results are shown in FIGS. 9A-9D. This diagram is a SPR sensorgram of the detected interaction between each of the above three clones or Cont-68 for control and NF-κB p50.

The single-stranded DNA variants free from a sequence comprising the 5'-terminal primer-binding region of each NF-κB p50-binding DNA aptamer tested in Example 2 had binding ability of Kd=5.7 to 8.7 pM (FIGS. 8 and 9). By contrast, the control hairpin-shaped DNA Cont-68 having the natural DNA sequence in the stem had binding ability of Kd=3.5 nM, which was close to conventionally known values (FIGS. 8 and 9). These results demonstrated that the DNA aptamer containing a double-stranded region comprising non-Watson-Crick base pairs, obtained by the production method of the present invention, has binding ability Example 4: Binding Ability of NF-κB p50-Binding DNA Aptamer Variant 5R01-68 for NF-κB p50>

The consensus structures of the clones of NF-κB p50-binding DNA aptamers obtained in Example 1 comprise, as mentioned above, non-Watson-Crick base pairs which are not found in usual double-stranded DNAs (FIG. 4). Thus, five non-Watson-Crick base pairs, i.e., two G-T base pairs and three G-A base pairs, present in the double-stranded region of 5R01-68 prepared in Example 3 as a variant of the NF-κB p50-binding DNA aptamer 5R01 were all changed to G-C base pairs serving as Watson-Crick base pairs. The NF-κB p50-binding ability of the resulting variant 5R01mut-68 (SEQ ID NO: 35) was determined by the SPR method.

(Method)

The variant 5R01mut-68 was prepared by chemical synthesis on the basis of the nucleotide sequences represented by SEQ ID NO: 35. This variant was tested for its NF-κB p50-binding ability in the same way as in Example 2. Also, 5R01-68 comprising non-Watson-Crick base pairs and Cont-68 were used as controls and tested for their binding ability in the same way as above.

(Results)

The results are shown in FIGS. 10A-10C. This diagram is a SPR sensorgram of the detected interaction between the variant 5R01mut-68 (FIG. 10A) or the control 5R01-68 (FIG. 10B) or Cont-68 (FIG. 10C) and NF-κB p50. The variant 5R01mut-68 had binding ability at least 20 times stronger than that of Cont-68, but had a dissociation rate constant 10 times larger than that of 5R01-68 and was thus confirmed to be more easily dissociated from NF-κB p50 than 5R01-68 having non-Watson-Crick base pairs. These results demonstrated that the non-Watson-Crick base pairs in the consensus structure of each NF-κB p50-binding DNA aptamer clone obtained by the production method of the present invention contribute to binding with NF-κB p50.

Example 5: Binding Specificity of NF-κB p50-Binding DNA Aptamer for NF-κB p50

The NF-κB p50-binding DNA aptamers obtained in Example 1 were examined for their NF-κB p50 binding selectivity.

(Method)

5R01-68 having non-Watson-Crick base pairs (prepared in Example 3) and 5R01mut-68 free from non-Watson-Crick base pairs (prepared in Example 4) were immobilized on sensor chips, which were in turn used to test their binding to a transcriptional factor other than NF-κB p50, i.e., AP-1 protein (Promega Corp.), and Taq DNA polymerase (F. Hoffmann-La Roche Ltd.; 1 U=0.05 pmol) by the SPR method.

A 59-mer DNA fragment Taq-59 (SEQ ID NO: 36) containing an anti-Taq DNA aptamer known in the art was prepared as a control aptamer by chemical synthesis and tested for its binding to various proteins, as in 5R01-68 and 5R01mut-68.

(Results)

The results are shown in FIGS. 11A-11C. This diagram is a SPR sensorgram of the detected interaction between 5R01-68 (FIG. 11A), 5R01mut-68 (FIG. 11B), or Taq-59 for control and NF-κB p50 (filled circle), Taq DNA polymerase (open circle), or AP-1 (open triangle). This diagram shows that 5R01-68 and 5R01mut-68 have very weak binding ability for AP-1 or Taq DNA polymerase, demonstrating that the DNA aptamer obtained by the production method of the present invention is capable of specifically binding to the target substance NF-κB p50.

Table 2 summarizes the dissociation constants (Kd) for NF-κB p50 of the DNA aptamers, etc. tested in each Example, which were calculated from the results of the SPR method.

TABLE 2

| DNA | $K_d$ (M) |
| --- | --- |
| 5R01 | $3.5 \times 10^{-12}$ |
| 5R01-68 | $5.4 \times 10^{-12}$ |
| 5R01mut-68 | $1.4 \times 10^{-10}$ |
| 5R14 | $6.6 \times 10^{-12}$ |
| 5R14-68 | $8.7 \times 10^{-12}$ |
| 5R05 | $2.1 \times 10^{-12}$ |
| 5R05-68 | $7.2 \times 10^{-12}$ |
| Cont-68 | $3.5 \times 10^{-9}$ |
| Taq-59 | $\gg 10^{-9}$ |

All publications, patents, and patent applications cited herein are incorporated herein by reference in their entirety.

The invention claimed is:

1. A nucleic acid molecule that binds to a target substance, wherein the nucleic acid molecule comprises one or more double-stranded regions each consisting of a pair of regions each comprising 5 to 20 consecutive bases wherein the regions are base-paired to each other to form a duplex of 5 to 20 base pairs;

wherein at least one of the double-stranded regions comprises 1 to 10 base pairs consisting of non-Watson-Crick base pairs;

wherein the target substance is NF-κβ p50, and the nucleic acid molecule comprises a double-stranded region consisting of the nucleotide sequences represented by SEQ ID NOs: 1 and 2.

2. The nucleic acid molecule according to claim 1, wherein the nucleic acid molecule consists of a single-stranded nucleic acid or a double-stranded nucleic acid.

3. The nucleic acid molecule according to claim 2, wherein the nucleic acid molecule is a DNA.

4. The nucleic acid molecule according to claim 1, wherein the nucleic acid molecule comprises a double-stranded region consisting of the nucleotide sequences represented by SEQ ID NOs: 3 and 4, SEQ ID NOs: 5 and 6, or SEQ ID NOs: 7 and 8.

5. The nucleic acid molecule according to claim 4, wherein the nucleic acid molecule comprises the nucleotide sequence represented by any of SEQ ID NOs: 9 to 21.

6. A method of inhibiting the function of NF-κβ p50 comprising contacting NF-κβ p50 with a composition comprising the nucleic acid molecule according to claim 1 as an active ingredient.

7. A pharmaceutical composition comprising an inhibitor of NF-κβ p50 function according to claim 6.

8. A kit for NF-κβ p50 detection comprising at least one nucleic acid molecule according to claim 1.

* * * * *